US012685784B2

(12) United States Patent
Lee et al.

(10) Patent No.: US 12,685,784 B2
(45) Date of Patent: Jul. 21, 2026

(54) POLYMER-CARGO-COMPLEXES COMPRISING CROSS-LINKED COPOLYMERS AND CARGO MOLECULES

(71) Applicant: HELMHOLTZ-ZENTRUM FÜR INFEKTIONSFORSCHUNG GMBH, Braunschweig (DE)

(72) Inventors: Sangeun Lee, Saarbrücken (DE); Brigitta Loretz, Saarbrücken (DE); Claus-Michael Lehr, Saarbrücken (DE); K.H. Anna Hirsch, Saarbrücken (DE)

(73) Assignee: Helmholtz-Zentrum für Infektionsforschung GmbH, Braunschweig (DE)

(*) Notice: Subject to any disclaimer, the term of this patent is extended or adjusted under 35 U.S.C. 154(b) by 734 days.

(21) Appl. No.: 18/011,716

(22) PCT Filed: Jun. 18, 2021

(86) PCT No.: PCT/EP2021/066600

§ 371 (c)(1),
(2) Date: Dec. 20, 2022

(87) PCT Pub. No.: WO2021/259783

PCT Pub. Date: Dec. 30, 2021

(65) Prior Publication Data

US 2023/0285590 A1 Sep. 14, 2023

(30) Foreign Application Priority Data

Jun. 23, 2020 (EP) .................................... 20181734

(51) Int. Cl.
*A61K 47/69* (2017.01)
*A61K 48/00* (2006.01)

(52) U.S. Cl.
CPC ...... *A61K 47/6935* (2017.08); *A61K 48/0041* (2013.01)

(58) Field of Classification Search
None
See application file for complete search history.

(56) References Cited

FOREIGN PATENT DOCUMENTS

WO WO-2013113501 A1 * 8/2013 ............. A61P 35/00

OTHER PUBLICATIONS

Kölmel, D. K., & Kool, E. T. (2017). Oximes and Hydrazones in Bioconjugation: Mechanism and Catalysis. Chemical reviews, 117(15), 10358-10376. https://doi.org/10.1021/acs.chemrev.7b00090 (Year: 2017).*

Bouillon et al. (2018). Biomolecular Dynamic Covalent Polymers for DNA complexation and siRNA delivery. Journal of Materials Chemistry B. 6. 10.1039/C8TB01278D. (Year: 2018).*

Thakur G, Rodrigues FC, Singh K. Crosslinking Biopolymers for Advanced Drug Delivery and Tissue Engineering Applications. Adv Exp Med Biol. 2018; 1078:213-231. doi: 10.1007/978-981-13-0950-2_11. PMID: 30357625. (Year: 2018).*

Lee, Sangeun & K., Cansu & Jang, Hongje & Koch, Marcus & Loretz, Brigitta & Buhler, Eric & Lehr, Claus-Michael & Hirsch, Anna. (2020). pH-Dependent Morphology and Optical Properties of Lysine-Derived Molecular Biodynamer. Materials Chemistry Frontiers. 4. 10.1039/C9QM00651F. (Year: 2019).*

Bouillon, C., Biomolecular dynamic covalent polymers for DNA complexation and siRNA delivery, Journal of Materials Chemistry B, Jan. 1, 2018, pp. 7239-7246, vol. 6, No. 44, XP055758042, The Royal Society of Chemistry.

Bouillon, C., Supporting Information Biomolecular Dynamic Covalent Polymers for DNA complexation and siRNA delivery, Nov. 28, 2018, URL:http://www.rsc.org/suppdata/c8/tb/c8tb01278d/c8tb01278d1.pdf, XP055758102, The Royal Socieity of Chemistry.

Lee, S, pH-Dependent morphology and optical properties of lysine-derived molecular biodynamers, Materials Chemistry Frontiers, Mar. 5, 2020, pp. 905-909, vol. 4, No. 3, Royal Society of Chemistry, XP055758055.

Liu, Y., Proteoid Dynamers with Tunable Properties, Advanced Functional Materials, Sep. 1, 2016, pp. 6297-6305, vol. 26, No. 34, XP055758057, Wiley-VCH Verlag GmbH & Co. KGaA.

Hirsch, A., Biodynamers: Self-Organization-Driven Formation of Doubly Dynamic Proteoids, Journal of the American Chemical Society, Feb. 21, 2012, pp. 4177-4183, vol. 134, No. 9, ACS Publications, XP055758061.

Sreenivasachary, N., DyNAs: Constitutional Dynamic Nucleic Acid Analogues, Chemistry A European Journal, DE, Jan. 1, 2006, pp. 8581-8588, vol. 12, No. 33, Wiley-VCH Verlag GmbH & Co. KGaA, XP8121658.

* cited by examiner

*Primary Examiner* — Robert A Wax
*Assistant Examiner* — Julia A. Rossi
(74) *Attorney, Agent, or Firm* — Hudak, Shunk & Farine Co. LPA

(57) ABSTRACT

Polymer-cargo-complexes including cross-linked copolymers and cargo molecules bound to the copolymers by electrostatic interactions. The non-medical use thereof for transfection and to a kit including such polymer-cargo-complexes. The polymer-cargo-complexes for use in therapy, in particular for use in gene therapy or peptide/protein drug delivery. A method of preparing the polymer-cargo-complexes. A kit for preparing a polymer-cargo-complex of the invention.

14 Claims, 9 Drawing Sheets

8A

8B

POLYMER-CARGO-COMPLEXES COMPRISING CROSS-LINKED COPOLYMERS AND CARGO MOLECULES

FIELD OF THE INVENTION

The present invention relates to polymer-cargo-complexes comprising cross-linked copolymers and cargo molecules bound to the copolymers by electrostatic interactions. The invention further relates to the non-medical use thereof for transfection and to a kit comprising such polymer-cargo-complexes. The present invention further relates to the polymer-cargo-complexes for use in therapy, in particular for use in gene therapy or peptide/protein drug delivery. The invention also relates to a method of preparing the polymer-cargo-complexes. The present invention also relates to a kit for preparing a polymer-cargo-complex of the invention.

BACKGROUND OF THE INVENTION

Dynamers are polymers using dynamic covalent chemistry principles. Molecular dynamers are polymerized via reversible covalent bonds and exist as an equilibrium polymer with inherent potential of reversibility and stimuli-responsiveness on triggers. Using bio-based monomers like amino-acid-derivatives dynamic analogues proteins (proteoids) can be generated. This interesting type of new polymers was, however, rarely studied for cargo delivery applications such as drug delivery.

Gene therapy is a disease treatment approach replacing abnormal genes or adding new functions, by injecting nucleic acids into the disease cells. This therapy is an advanced treatment for intractable diseases such as cancers, and genetic disorders because it enables eliminating the underlying causes of the diseases. Against expectations, however, it was in a stalemate for the last decades due to the limitations of the gene transfection vectors, such as gene transfection efficiency, toxicity, and immunogenicity.

Gene transfection vector is a crucial requirement of gene therapy and defines its success. Nucleic acids are easily degradable in the physiological condition by deoxyribonuclease or ribonucleases. Considering these enzymes (nucleases) are located in the extracellular environments, the nucleic acids need to be protected from the nucleases until they reach the target cells. Moreover, negative charges of the nucleic acids inhibit their diffusion into the cells across the cell membranes. Accordingly, transfection vectors are essential to deliver nucleic acids into the cytoplasm while protecting them from the nucleases. In the present disclosure the term "nucleic acids" collectively refers to oligonucleotides (in particular up to 20 bp) and polynucleotides (in particular from more than 20 bp up to 200,000 bp) such as DNA and RNA, in particular to mRNA, plasmids, self-amplifying RNAs, CRISPR/Cas systems and/or smaller nucleic acids such as antisense oligo nucleotides, siRNA, miRNA.

Transfection vectors are classified into viral vectors (retroviruses; adenoviruses, adenoassociated virus, etc.) and non-viral vectors (cationic lipids, dendrimers, peptides, and polymers). Although the viral vectors have high transmission efficiency and long gene expression, critical issues, such as insertional mutagenesis, immunogenicity, and low production efficiency, restrict their applications. Thus, non-viral vectors have attracted more attention, due to the lower safety concerns and easier fabrications with low cost than viral vectors.

Among the non-viral vectors, cationic polymers, especially poly(ethylene imine) (PEI), have superior properties as a gene delivery carrier, including 1) efficient condensation and stabilization of nucleic acids, 2) high cellular uptake and transfection efficiency, water solubility, and easy production and modifications. The positively charged PEI forms a complex (polyplex) with negatively charged nucleic acids by electrostatic interaction. The term "polyplex" generally refers to any complex of a polymer and DNA. The formed polyplex prevents nucleic acid degradation by the nucleases. In addition, there is efficient cellular uptake of the polyplexes by endocytosis. Uptaken polyplexes release nucleic acids into the cytoplasm by endosomal escape. Although the exact mechanism of the endosomal escape of the polyplexes is unclear, a "proton sponge effect" is commonly accepted to explain the phenomena. This effect hypothesizes that the PEI/gene complex destabilizes the acidic pH of endosomes, and eventually escapes from there. The endosomal escape of the polyplexes by the proton sponge effect is considered supporting high transfection efficiency of the PEI polyplexes. These remarkable properties of PEI made it as "a gold standard" of polymeric transfection agents.

Aforementioned features of PEI (nucleic acid stabilization via tight condensation, high transfection efficiencies, and efficient cellular uptake) made it a promising gene transfection agent. However, the PEI is in a huge dilemma; the high transfection efficiency strongly correlates with its high cytotoxicity. Many of researches report that the cationic PEI damages cellular membranes and induces cell apoptosis. Not only the PEI, other cationic polymers such as poly-L-lysine (PLL), poly(2-dimethylaminoethyl methacrylate), cationic polysaccharides, are also not completely free from the cytotoxicity problem. Thus, cellular toxicity of cationic polymers remains as a challenge in this field.

Furthermore, proteins and smaller peptides are attracting more attention as potential therapeutics for various human diseases. However, their poor stability and availability in the body inhibit their use as therapeutic medicines. When the therapeutics are administered via parenteral administration, the most common way for peptide and protein drugs, they need to permeate cell layers. The large molecular size, charge, hydrophilicity, and low stability of the proteins are additional challenges that need to be considered to overcome those barriers. On the other hand, oral administration, known as the most patient-friendly administration, has other severe limitations such as degradation by proteolytic enzymes secreted by the digestive organs. Therefore, delivery strategies are required to overcome those limitations and reach the targets. A successful protein drug delivery system protects proteins/peptides from enzymatic degradation as well as improves their absorption, not altering biological activity.

SUMMARY OF THE INVENTION

It is therefore an object of the present invention to overcome the disadvantages of the prior art. The problem is solved by the subject-matter of the claims.

The problem is in particular solved by polymer-cargo-complexes comprising a) a cross-linked copolymer, the copolymer comprising two alternating units A and B forming a repeat unit A-B such that the copolymer comprises a $(A\text{-}B)_n$ backbone with n being the number of repeat units of the backbone, wherein unit A is a derivative of an amino acid hydrazide and unit B is a derivate of a dialdehyde comprising a polyethylene glycol (PEG) group,
   wherein 40 to 100 mol % (for example 50 to 99.9 mol %, 60 to 99 mol %, 70 to 98 mol %, 80 to 95 mol % or 85 to 90 mol %) of unit A are derivatives of hydrazides of either cationic amino acids selected from the group consisting of lysine (Lys), arginine (Arg), histidine (His) and combinations of two or more thereof, or anionic amino acids selected from the group consisting of aspartic acid (Asp), glutamic acid (Glu) and combinations thereof, wherein the copolymer comprises imine groups and acylhydrazone groups alternatingly linking together the alternating units A and B of the polymer backbone such that the units A and B of the backbone are each linked to one neighboring unit by an imine group and to the other neighboring unit by an acylhydrazone group, and b) cargo molecules bound to the cross-linked copolymer by electrostatic interactions between the cargo molecules and the amino acid side chains of unit A.

Molecular biodynamer (BDy) is a novel polymer concept having both advantages of biopolymers and dynamic covalent chemistry. Dynamic covalent bond is a reversible covalent bond under specific conditions such as pH and temperature. Based on the dynamic reversibility of the covalent bond, it has applied for the development of stimuli-responsive systems and self-healing material. Molecular dynamer is a polymer formed by the dynamic covalent bonds. Therefore, the polymerization and degradation of the molecular dynamer are reversible under specific conditions. Moreover, when the polymeric component mimics biological polymers such as nucleic acids, peptides, and polysaccharides, these molecular dynamers supposed to have biopolymer's advantages (biocompatibility, biodegradability, and biofunctionality), and called "molecular biodynamers" or "biodynamers".

Hirsch and coworkers reported following molecular biodynamers (Yun Liu, Marc C. A. Stuart, Eric Buhler and Anna K. H. Hirsch, Proteoid Dynamers with Tunable Properties, *Advanced Functional Materials,* 26, 34, (6297-6305), (2016)).

$R_1$ is the side chain of amino acids, such as lysine, histidine and arginine. According to the present invention, 40 to 100 mol % (for example 50 to 99.9 mol %, 60 to 99 mol %, 70 to 98 mol %, 60 to 95 mol % or 85 to 90 mol %) are either cationic amino acids selected from the group consisting of lysine (Lys), arginine (Arg), histidine (His) and combinations of two or more thereof, or anionic amino acids selected from the group consisting of aspartic acid (Asp), glutamic acid (Glu) and combinations thereof. Component B is an ethylene glycol conjugated dialdehyde such as hexaethylene glycol conjugated carbazole dialdehyde. $R_2$ is preferably selected from the group consisting of a carbazole, pyrole derivatives (e.g. 2,5-dimethylpyrrole), benzyl group, and alkyl group. Preferably, m is in a range of from 3 to 12, more preferably from 4 to 10, more preferably from 5 to 8. More preferably, m equals 6.

In scheme 2 shown above, components A and B (on the left hand side) give rise to units A and B of the copolymer. The copolymer is shown on the right hand side (units A and B not indicated).

These polymers are preferably composed of cationic amino acid-derivatives (e.g. Lys, His, Arg) with hydrazide and ethylene glycol grafted dialdehydes (e.g. carbazole dicarboxaldehyde with hexaethylene glycol). The applications of these polymers in the biomedical area have not been evaluated so far.

Presently, it was now found that respective polymers can be transformed into a potential tool for delivery of polynucleotides and/or oligonucleotides into eukaryotic cells in both therapeutic and non-therapeutic applications. Cationic Scheme 1

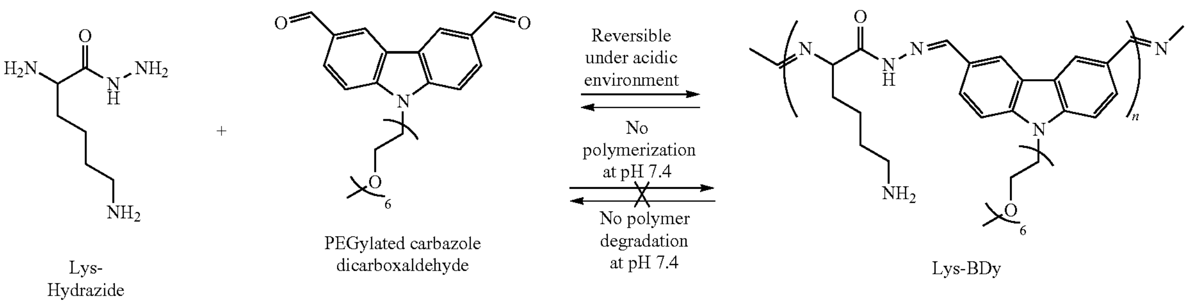

Lys-Hydrazide

PEGylated carbazole dicarboxaldehyde

Lys-BDy

However, such molecular biodynamers are generally not restricted to be based on Lys-Hydrazide and carbazole dicarboxaldehydes. The following scheme 2 shows the polymerization of molecular biodynamers in a more generalized way.

side amino acid side chains are particularly advantageous for delivery of nucleotides. Furthermore, delivery of other cargo is possible as well. For example, positively charged cargo molecules may be bound to the polymers comprising negatively charged side chains, for example based on aspartic Scheme 2

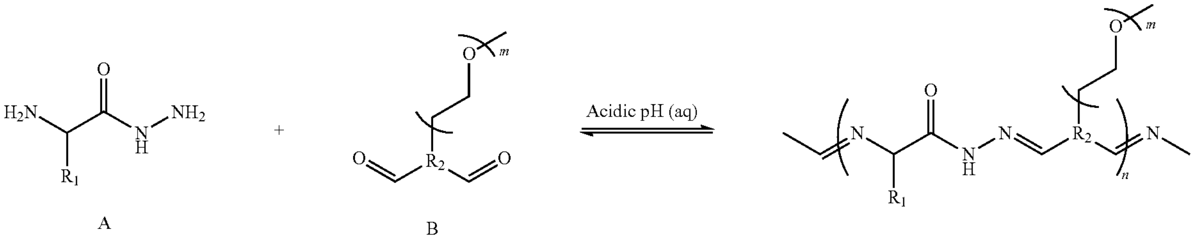

A

B acid or glutamic acid. However, the pre-described polymers as such are not useful for any of these applications.

It was found that Lys-biodynamer formed a nano-complex with mRNA (mCherry) with a 10:1 N/P ratio. The N/P ratio (also referred to as NP ratio) is the molar ratio of amine groups (provided by the cationic amino acid derivatives) to phosphate groups (provided by the oligo- or polynucleotides). The formed complexes kept their nanostructures in deionized water, however, destabilized and dissociated immediately in saline solutions because electrostatic interactions between the mRNA and Lys-BDy were disturbed by ions in the saline. As cells require saline environments for survival both in vitro and in vivo, Lys-BDy turned out to be not suitable for delivery of nucleic acids into eukaryotic cells.

However, surprisingly it turned out that the complexes can be stabilized by cross-linking, for example cross-linking a fraction of the primary amines of the side chains of cationic amino acids. This measure surprisingly stabilized the complexes such that they did not dissociate immediately in saline solutions. The polyplex is up taken in a cell by endocytosis and localizes in an endosome. Due to the acidic pH of the endosome, the biodynamers degrade and the polyplex dissociates. Eventually, the loaded nucleic acids release into the cytoplasm. The polymerization is reversible under the acidic conditions because the BDy was formed by an equilibrium of acylhydrazone bond formation. This property was not deteriorated by cross-linking a fraction of amine groups of the cationic amino acids as acylhydrazone bond formation and dissociation was substantially not affected. Thus, the cross-linking approach surprisingly resulted in polymers that are on the one hand sufficiently stable in saline solutions and on the other hand sufficiently dissociating under acidic conditions for release of the nucleic acids after delivery into the cells.

In the polymer-cargo-complexes of the present invention, cargo molecules are bound to the cross-linked copolymer by electrostatic interactions between the cargo molecules and the amino acid side chains of unit A. In some embodiments, side chains of cationic amino acids are electrostatically interacting with anionic groups present on the cargo molecules. In some embodiments, side chains of anionic amino acids are electrostatically interacting with cationic groups present on the cargo molecules. In some embodiments, side chains of cationic amino acids are electrostatically interacting with anionic groups present on the cargo molecules and side chains of anionic amino acids are electrostatically interacting with cationic groups present on the cargo molecules.

Gene therapy has huge potential as a future remedy to treat intractable diseases. However, the lack of effective gene carriers limits the application of gene therapy. Although the polyplex formation using cationic polymers such as PEI and PLL is attractive due to their high stability and high efficiency, its high cytotoxicity remains a significant barrier. This disadvantage of the prior art is also overcome by the present invention as described in more detail below. In fact, the present invention shows remarkably lower toxicity than PEI or PLL.

In addition to the low cytotoxicity, various advantages of the invention were found including acid-responsive degradation, easy functionalization and modification, and polymerization in aqueous solution. These verified positive effects overcome the disadvantages of existing polymeric gene vectors suffering from high toxicity and low biodegradability.

The polymer-cargo-complexes of the invention are highly dynamically degradable upon a change in pH and require very few synthetic steps resulting in high yields and a highly efficient production. Furthermore, considering that higher pH sensitivity and degradability are closely related to biocompatibility, the chemical linkages of imines and acylhydrazones are highly advantageous for decreasing toxicity. Copolymers based on other chemical linkages are disadvantageous. For example, polymers connected using alternating oxime and acylhydrazone linkages (not imine and acylhydrazone linkages as in the present invention) are disadvantageous. Oximes and acylhydrazones have higher chemical stability over a broad pH range, making them less reversible than imines because of the mesomeric effect that reduces the electrophilicity of the original carbon-nitrogen double bond. Moreover, oximes are 1000 times less reversible than acylhydrazones and find application as click-chemistry for stable conjugation. Therefore, the polymer-cargo-complexes of the present invention are degraded faster by pH changes as compared to ones based on oximes. In addition, introduction of the oxime bond requires additional synthetic steps, modifying amine group to hydroxylamine group (also called amioxy group), which is not necessary for the polymer-cargo-complexes of the present invention.

The present invention relates to polymer-cargo-complexes comprising a) a cross-linked copolymer, the copolymer comprising two alternating units A and B forming a repeat unit A-B such that the copolymer comprises a $(A\text{-}B)_n$ backbone with n being the number of repeat units of the backbone, wherein unit A is a derivative of an amino acid hydrazide and unit B is a derivate of a dialdehyde comprising a polyethylene glycol (PEG) group,
   wherein 40 to 100 mol % (for example 50 to 99.9 mol %, 60 to 99 mol %, 70 to 98 mol %, 80 to 95 mol % or 85 to 90 mol %) of unit A are derivatives of hydrazides of either cationic amino acids selected from the group consisting of lysine (Lys), arginine (Arg), histidine (His) and combinations of two or more thereof, or anionic amino acids selected from the group consisting of aspartic acid (Asp), glutamic acid (Glu) and combinations thereof,
   wherein the copolymer comprises imine groups (IM) and acylhydrazone groups (HY) alternatingly linking together the alternating units A and B of the polymer backbone such that the units A and B of the backbone are each linked to one neighboring unit by an imine group and to the other neighboring unit by an acylhydrazone group, and
b) cargo molecules bound to the cross-linked copolymer by electrostatic interactions between the cargo molecules and the amino acid side chains of unit A.

The backbone of the copolymer of the invention may be depicted as . . . A-HY-BIM-A-HY . . . with A and B being the alternating units and IM and HY being the groups linking A and B together. Similarly, the backbone may of course also be depicted as . . . A-IM-B-HY-A-IM . . . . However, depiction as . . . A-HY-B-IM-A-HY . . . is preferred based on the scheme of Liu et al. (2016) presented above.

The number n of repeat units of the backbone is preferably in a range of from 50 to 500, more preferably from 65 to 375, more preferably from 80 to 250.

Preferably, the polymer-cargo-complexes of the invention are nanoparticles, in particular nanoparticles having a hydrodynamic diameter ($D_H$) in a range of from 50 nm to 350 nm, more preferably from 100 nm to 250 nm. The present invention also relates to a nanoparticle having a hydrodynamic diameter ($D_H$) in a range of from 50 nm to 350 nm, more preferably from 100 nm to 250 nm, wherein the nanoparticle comprises a polymer-cargo-complex of the present invention. Preferably, the indicated hydrodynamic diameter refers to nanoparticles in solution.

As described above, the copolymer comprises two alternating units A and B forming a repeat unit A-B such that the copolymer comprises a $(A-B)_n$ backbone with n being the number of repeat units of the backbone, wherein unit A is a derivative of an amino acid hydrazide and unit B is a derivate of a dialdehyde comprising a polyethylene glycol (PEG) group.

Unit A of the copolymer of the invention is a derivative of an amino acid hydrazide, in particular of an α-amino acid such as an L-α-amino acid. The amino acid may be selected from the group consisting of lysine (Lys), arginine (Arg), histidine (His) and combinations of two or more thereof. For example, a copolymer of the invention may comprise unit $A_K$ (based on Lys), unit $A_R$ (based on Arg) and unit $A_H$ (based on His). Notably, the invention is not restricted to derivatives of proteinogenic amino acids but may include non-proteinogenic amino acids such as ornithine. For example, unit A may the derivative of a naturally occurring cationic amino acid such as lysine, arginine, histidine and/or ornithine. Preferably, unit A is a derivative of a cationic amino acid hydrazide, the cationic amino acid preferably being selected from the group consisting of lysine, arginine, histidine and combinations of two or more thereof.

The hydrazide group of the monomeric precursor of unit A and one of the aldehyde groups of the monomeric dialdehyde precursor of unit B react to form the HY groups of the polymer of the invention.

In particular, unit A is a derivative of an amino acid hydrazide as shown in the following scheme 3.

Scheme 3

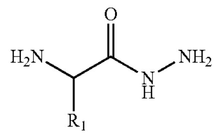

$R_1$ is an amino acid side chain.

The copolymer may be homogeneous regarding the amino acid side chain of unit A. For example, 100 mol % of the side chains of unit A may be the side chain of lysine (Lys), arginine (Arg), histidine (His), aspartic acid (Asp) or glutamic acid (Glu). However, the copolymer may also be heterogeneous regarding the amino acid side chain of unit A. For example, the copolymer may comprise units A having the side chain of lysine and units A having the side chain of arginine, for example in a total amount of from 40 to 100 mol % (for example 50 to 99.9 mol %, 60 to 99 mol %, 70 to 98 mol %, 80 to 95 mol % or 85 to 90 mol %) as compared to all amino acid side of the copolymer. The copolymer may also comprise units A having the side chain of lysine and units A having the side chain of histidine, for example in a total amount of from 40 to 100 mol % (for example 50 to 99.9 mol %, 60 to 99 mol %, 70 to 98 mol %, 80 to 95 mol % or 85 to 90 mol %) as compared to all amino acid side of the copolymer. The copolymer may also comprise units A having the side chain of arginine and units A having the side chain of histidine, for example in a total amount of from 40 to 100 mol % (for example 50 to 99.9 mol %, 60 to 99 mol %, 70 to 98 mol %, 80 to 95 mol % or 85 to 90 mol %) as compared to all amino acid side chains of the copolymer. The copolymer may also comprise units A having the side chain of lysine and units A having the side chain of arginine and units A having the side chain of histidine, for example in a total amount of from 40 to 100 mol % (for example 50 to 99.9 mol %, 60 to 99 mol %, 70 to 98 mol %, 80 to 95 mol % or 85 to 90 mol %) as compared to all amino acid side of the copolymer. The copolymer may also comprise units A having the side chain of aspartic acid and units A having the side chain of glutamic acid, for example in a total amount of from 40 to 100 mol % (for example 50 to 99.9 mol %, 60 to 99 mol %, 70 to 98 mol %, 80 to 95 mol % or 85 to 90 mol %) as compared to all amino acid side chains of the copolymer.

Basic side chains as the side chains of lysine, arginine and histidine are particularly advantageous for binding negatively charged cargo molecules, such as for example nucleic acids like DNA and/or RNA, in particular mRNA and/or siRNA. Acidic side chains are particularly advantageous for binding positively charged cargo molecules, for example positively charged peptides (for example oligopeptides or polypeptides such as proteins) or positively charged small molecules. In the present disclosure, the term “peptide” collectively refers to molecules comprising amino acids linked by peptide bonds. This includes oligopeptides (comprising up to 10 amino acid residues) and polypeptides (comprising more than 10 amino acid residues). Polypeptides comprising more than 50 amino acid residues may also be referred to as “proteins” according to the present invention. Thus, the term “peptides” as used herein includes proteins as well. Likewise, the term “peptide drugs” includes protein drugs.

Preferred nucleic acids cargo molecules are selected from the group consisting of antisense RNA, siRNA, miRNA, mRNA, pDNA. In some embodiments, nucleic acids are selected from the group consisting of mRNA, siRNA and combinations thereof. Preferred peptide cargo molecules are selected from the group consisting of peptide drugs (such as bleomycin, bortezomib, nesiritide), peptide antibiotics and antimicrobial peptides (naturally occurring (from mammalian, amphibians, insects, plants, bacteria, viruses); or synthetically produced), hormones (such as insulin)), enzymes (such as cas9), antibodies and antibody fragments.

According to the present invention, 40 to 100 mol %, for example 50 to 99.9 mol %, 60 to 99 mol %, 70 to 98 mol %, 80 to 95 mol %, or 85 to 90 mol % of unit A are derivatives of hydrazides of either cationic amino acids selected from the group consisting of lysine (Lys), arginine (Arg), histidine (His) and combinations of two or more thereof, or anionic amino acids selected from the group consisting of aspartic acid (Asp), glutamic acid (Glu) and combinations thereof.

The copolymer may comprise units A having side chains of other amino acids. Preferably, 0 to 60 mol %, for example 0.1 to 50 mol %, 1 to 40 mol %, 2 to 30 mol %, 5 to 20 mol %, or 10 to 15 mol % of unit A are derivatives of hydrazides of amino acids selected from the group consisting of serine (Ser), threonine (Thr), asparagine (Asn), glutamine (Gln), cysteine (Cys), glycine (Gly), proline (Pro), alanine (Ala), valine (Val), isoleucine (Ile), leucine (Leu), methionine (Met), phenylalanine (Phe), tyrosine (Tyr), tryptophan (Trp) and combinations of two or more thereof. Such amino acid side chains may for example be useful for adapting properties of the copolymer such as charges, crosslinking methods, hydrophobicity, interaction with cell-membrane, and for surface modification of the copolymer-cargo-complexes.

Unit B of the copolymer of the invention is a derivative of a dialdehyde. This enables formation of a copolymer of the invention comprising IM groups and HY groups alternatingly linking together the alternating units A and B of the polymer backbone. The two aldehyde groups lead to polymerization with the amino acid hydrazide so that a copolymer is formed. One aldehyde group forms an imine group with the a-amino group of the amino acid hydrazide. The other aldehyde group forms an acylhydrazone group with the hydrazide group of the amino acid hydrazide. Thus, the IM groups of the copolymer are preferably formed by reaction of an amino group of the amino acid hydrazide, in particular of the alpha amino group, with one of the aldehyde groups of the dialdehyde. The alpha amino group is the amino group on the Co carbon atom, i.e. on the carbon atom directly adjacent to the hydrazide group. The HY groups of the copolymer are preferably formed by reaction of the other aldehyde group of the dialdehyde with the hydrazide group of the amino acid hydrazide.

Unit B of the copolymer of the invention is a derivate of a dialdehyde comprising a polyethylene glycol (PEG) group. Preferably, unit B of the copolymer of the invention comprises a carbazole group. In other words, unit B is preferably the derivative of a carbazole dialdehyde comprising a PEG group.

Preferably, the dialdehyde derivative comprises a PEG chain having from 3 to 12 units, more preferred from 4 to 10 units, more preferred from 5 to 8 units. Hexaethylene glycol ($PEG_6$) is most preferred. PEG further reduces cytotoxicity and stabilizes the polyplex. Furthermore, PEG increases the water solubility of the monomeric dialdehydes used for copolymer formation, in particular of monomeric carbazole derivatives such as in particular carbazole dicarboxaldehydes preferably used for copolymer formation.

In particular, unit B is a derivative of a dialdehyde comprising a polyethylene glycol (PEG) group as shown in the following scheme 4.

Scheme 4

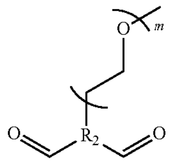

$R_2$ is preferably selected from the group consisting of a carbazole, pyrole derivatives (e.g. 2,5-dimethylpyrrole), benzyl group, and alkyl group. Carbazole is most preferred.

Unit B is a derivate of a dialdehyde comprising a polyethylene glycol (PEG) group. The PEG group further reduces cytotoxicity and stabilizes the polymer-cargo-complex. Furthermore, PEG increases the water solubility of the monomeric dialdehydes used for copolymer formation. Preferably, the PEG group is a PEG chain having from 3 to 12 units. Thus, the number m of units in the PEG chain is preferably in a range of from 3 to 12, more preferably from 4 to 10, more preferably from 5 to 8. More preferably, m equals 6.

The copolymer may be heterogeneous with respect to unit B. For example, the copolymer may comprise units B with $R_2$ being carbazole and other units B with $R_2$ being a pyrole derivative (e.g. 2,5-dimethylpyrrole), benzyl group, and/or alkyl group. However, preferably units B of the copolymer are homogeneous with respect to $R_2$, i.e. $R_2$ is the same for all units B of the copolymer.

The copolymer may also be heterogeneous with respect to the PEG groups of unit B. For example, the copolymer may comprise units B with a PEG chain having 6 units and other units B with a PEG group having 3 or 4 or 8 or 12 units. However, preferably units B of the copolymer are homogeneous with respect to the PEG group, i.e. the number of units of the PEG chain is the same for all units B of the copolymer.

Preferably, unit B is a derivative of hexa-ethylene glycol conjugated dialdehyde, in particular of hexa-ethylene glycol conjugated carbazole dialdehyde, preferably of hexa-ethylene glycol conjugated carbazole dicarboxaldehyde as shown in the following scheme 5.

Scheme 5

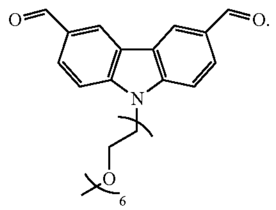

Preferably, the copolymer is based on polymerization of hydrazides of cationic amino acids with carbazole dicarboxaldehydes.

The polymer-cargo-complexes of the invention comprise a cross-linked copolymer. This may in other words also be described as the copolymer comprising cross-linking groups (XL). Cross-linking here includes both chemical cross-linking by covalent bonds, and physical cross-linking by hydrophobic interactions, hydrogen bonds, electrostatic interactions and combinations of two or more thereof. Preferably, the copolymer comprises cross-linking groups linking together distinct units A such that one cross-linking group links together two units A. In particular, the copolymer is preferably cross-linked by cross-linking groups linking together distinct units A such that one cross-linking group links together two units A. The cross-linking groups may link together units A within a single backbone (intra-backbone cross-links) and/or units A being present in different backbones (inter-backbone cross-links).

Preferably, the ratio of the total number of cross-linking groups to the total number of units A of the polymer is in a range of from 0.05:1 to 0.45:1. The ratio is preferably not very low because otherwise the stabilizing effect of the cross-linking groups is very low. On the other hand, the ratio is preferably not very high because otherwise biodegradability may be low. Therefore, it is advantageous to keep the ratio of the total number of cross-linking groups to the total number of units A of the polymer in a range of from 0.05:1 to 0.45:1, more preferred from 0.10 to 0.40.

Preferably, the cross-linking group (XL) links together the amino acid side chains ($R_1$) of two units A, for example as shown in the following Scheme 6.

Scheme 6

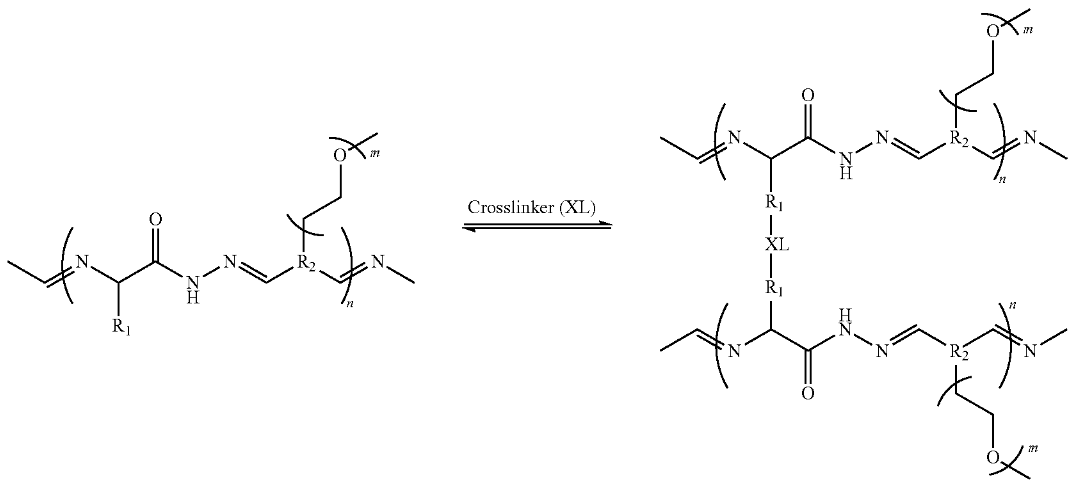

Preferably, the cross-linking group is a diimine group. The following scheme 7 exemplarily shows a cross-linking group linking together two units A in a copolymer of the invention. The copolymer shown is the particularly preferred Lys-BDy already described above. The amino groups of two lysine derivatives of the copolymer have been cross-linked by glutaraldehyde such that a diimine cross-linking group was formed.

Scheme 7

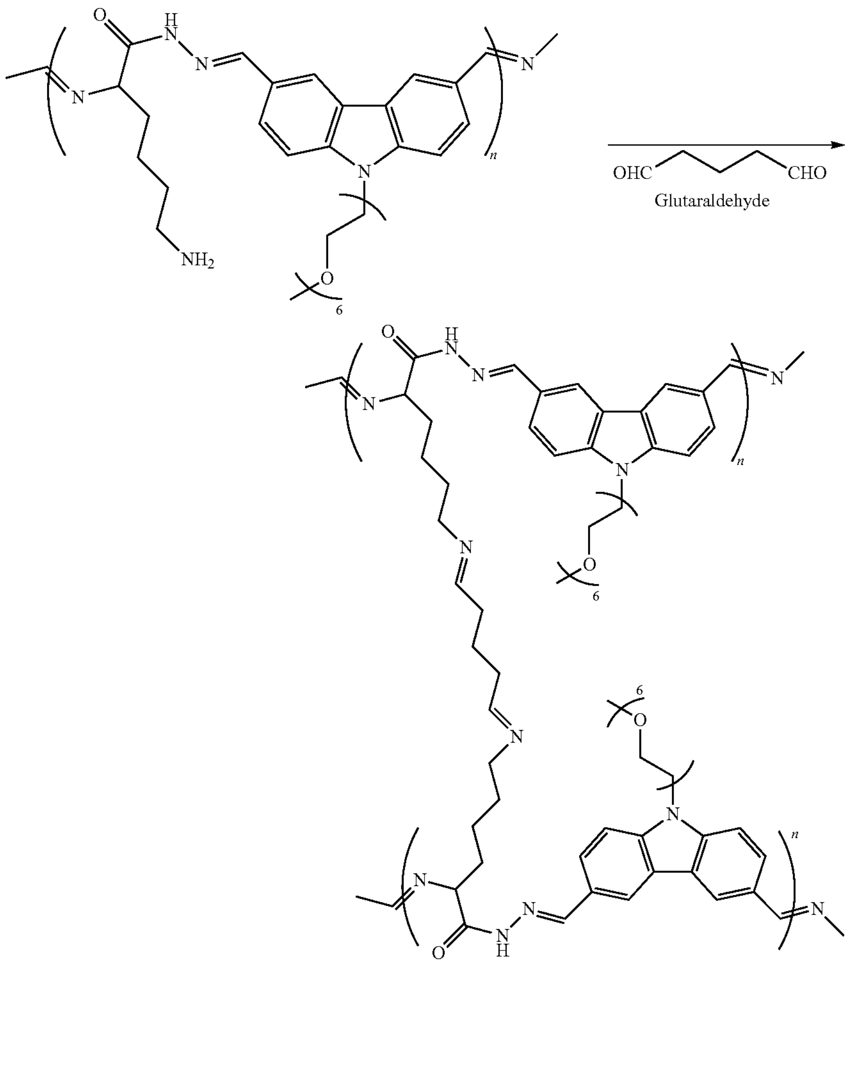

There may be heterogeneous cross-links, i.e. cross-linking groups linking together two amino acid side chains that are not of the same type. For example, a cross-linking group may link together a glutamic acid side chain and a lysine side chain. There may also be homogeneous cross-links, i.e. cross-linking groups linking together two amino acid side chains of the same type. For example, a cross-linking group may link together two lysine side chains or two cysteine side chains. Two cysteine side chains may be linked together to form a disulfide bond. In particular, the cross-linked copolymer may comprise both heterogeneous cross-links and homogeneous cross-links. It is also possible that a cross-linked copolymer comprises only heterogeneous cross-links or alternatively only homogeneous cross-links.

Generally, there is a great variety of cross-linking groups. In particular, cross-linking groups may be different depending on the amino acid side chains that are cross-linked. Both chemical cross-linking and physical cross-linking are available for this purpose. Diimine groups are preferred cross-linking groups of the invention.

For example, the copolymer may comprise amine-specific cross-linking groups. These are cross-linking groups that link together amine groups, in particular amino groups of amino acid side chains such as lysine and/or arginine. Amine-specific cross-linking groups are preferably diimine groups.

In some embodiments, cross-linking may be physical cross-linking, in particular cross-linking by hydrophobic interactions, electrostatic interactions, salt-bridges, host-guest interactions, hydrogen bonds between the amino acid side chains or combinations of two or more thereof. For example, physical cross-linking is possible by incorporating relatively hydrophobic amino acids, such as tryptophan (Trp), phenylalanine (Phe) and/or tyrosine (Tyr). Such amino acids may provide physical cross-linking by hydrophobic interactions. Preferably, 0 to 60 mol %, for example 0.1 to 50 mol %, 1 to 40 mol %, 2 to 30 mol %, 5 to 20 mol %, or 10 to 15 mol % of unit A are derivatives of hydrazides of amino acids selected from the group consisting of phenylalanine (Phe), tyrosine (Tyr), tryptophan (Trp) and combinations of two or more thereof.

The copolymer may also comprise cross-linking groups specific for nucleophilic amino acid side chains such as for example lysine, cysteine, serine, threonine and/or tyrosine. As described above, in case of cysteine, the cross-linking group may comprise a disulfide bond.

Using a system without crosslinking is problematic because the particles are not stable in vivo. To improve the stability of polymer-cargo-complexes, the invention uses a combination of crosslinking and pH-degradable polymers. Crosslinking is stabilizing polymeric materials. However, in the case of transfection agents, crosslinking was avoided so far because crosslinking inhibited cargo release from the stabilized system. The crosslinking of the present invention is unique in both stabilizing the system but overcoming the limitations of crosslinking with reversible chemical linkages ensuring degradation of the polymer and thus cargo release.

The polymer-cargo-complex of the invention comprises cargo molecules bound to the cross-linked copolymer by electrostatic interactions between the cargo molecules and the amino acid side chains of unit A. Preferably, the cargo molecule is selected from the group consisting of nucleic acid cargo molecules and peptide cargo molecules. Preferred nucleic acids are selected from the group consisting of antisense RNA, siRNA, miRNA, mRNA and pDNA. In some embodiments, nucleic acids are selected from the group consisting of mRNA, siRNA and combinations thereof. Preferred peptides are selected from the group consisting of peptide drugs (e.g., bleomycin, nesiritide), hormones (e.g., insulin), enzymes (e.g., cas9), antibodies (e.g., murine monoclonal antibodies, chimeric monoclonal antibodies, humanized monoclonal antibodies, human monoclonal antibodies), and antibody fragments (e.g., immune globulins, immune Fabs).

Proteins and smaller peptides are getting more attention as potential therapeutics for various human diseases. The term "peptide" may refer to a short amino acid chain, in particular having a specific function such as leuprolide, polymyxin, or glutathione. However, the term "peptide" also includes larger peptides, for example polypeptides and in particular proteins, i.e. polypeptides having more than 50 amino acid residues. In some embodiments, the term "protein" may refer to a natural polypeptide folding into three-dimensional structures like hormones (e.g., insulin), antibodies, and antibody fragments. These peptides or proteins drugs are more disease-specific and effective with smaller doses to get desired therapeutic effects comparing to conventional molecular medicines. Therefore, they are potent candidates drawing FDA-approval, and commercialization, for chronic diseases such as cancer, diabetes, leukemia, and rheumatism.

However, their poor stability and availability in the body inhibit their use as therapeutic medicines. When the therapeutics are administered via parenteral administration, the most common way for peptide and protein drugs, they need to permeate cell layers. The large molecular size, charge, hydrophilicity, and low stability of the proteins are additional challenges that need to be considered to overcome those barriers. On the other hand, oral administration, known as the most patient-friendly administration, has other severe limitations such as degradation by proteolytic enzymes secreted by the digestive organs.

Therefore, delivery strategies are required to overcome those limitations and reach the targets. A successful protein drug delivery system protects proteins/peptides from enzymatic degradation as well as improves their absorption, not altering biological activity.

In this invention, we have demonstrated protein delivery using biodynamers. As a model drug, fluorescein isothiocyanate conjugated albumin complexed with lysine-biodynamers. The polymer-cargo-complexes were formed with a hydrodynamic size of 244 nm (FIG. 5B) and spherical shape (observed by transmission electron microscopy, TEM).

The electrostatic interactions may be formed between positively charged amino acid side chains of unit A (for example lysine, arginine and/or histidine side chains) and negatively charged cargo molecules, in particular nucleic acids. The electrostatic interactions may also be formed between negatively charged amino acid side chains of unit A (for example aspartic acid side chains and/or glutamic acid side chains) and positively charged cargo molecules. Of course, a negatively charged cargo molecule may comprise positive charges as well and a positively charged cargo molecule may comprise negative charges as well, provided that those do not interfere with the electrostatic interaction with the amino acid side chains of unit A. Thus, the terms "negatively charged cargo molecules" and "positively charged cargo molecule" refer to the respective net charges, in particular to net surface charges. Notably, for the electrostatic interaction to be formed it is not even necessary that the net charge or surface net charge of the cargo molecule is opposite as compared to the amino acid side chains of unit A. It may be sufficient that there is just a local net surface charge on the cargo molecule that enables the electrostatic interaction. For example, a cargo molecule may have a part of its surface with net positive surface charge and another part of its surface with net negative surface charge. Such a cargo molecule may bind to negatively charged amino acid side chains of unit A with its surface part that has a net positive surface charge. On the other hand, such a cargo molecule may bind to positively charged amino acid side chains of unit A with its surface part that has a net negative surface charge.

Nucleic acids are preferred cargo molecules. Preferably, the cargo molecules are selected from the group consisting of oligonucleotides (for example comprising from 5 to 30 nucleotides, in particular from 10 to 25 or from 15 to 20 nucleotides) and polynucleotides (preferably comprising from more than 30 nucleotides to 10,000 nucleotides, for example from 50 to 5,000 nucleotides, from 100 to 3,000 nucleotides or from 500 to 1,000 nucleotides) of DNA and/or RNA, in particular mRNA, plasmids, self-amplifying RNAs, CRISPR/Cas systems, antisense oligo nucleotides, siRNA, miRNA and combinations of two or more thereof. In some embodiments, nucleic acids are selected from the group consisting of mRNA, siRNA and combinations thereof. In some embodiments, the cargo molecules may be even larger nucleic acids, for example DNA having up to $5.0\times10^9$ base pairs or pDNA having from 200,000 to 800, 000 nucleotides, for example around 400,000 nucleotides (i.e. around 200,000 base pairs).

The present invention relates to polymer-cargo-complexes, in particular to polyplexes comprising cross-linked copolymers and nucleic acids. Preferably, the polymer-cargo-complexes of the invention are nanoparticles, in particular nanoparticles having a Z-average hydrodynamic diameter ($D_H$) in a range of from 50 nm to 350 nm, more preferably from 75 nm to 300 nm, for example from 100 nm to 250 nm, from 100 nm to 200 nm, or from 100 nm to 150 nm, Preferably, the Z-average hydrodynamic diameter is determined by dynamic light scattering (DLS).

The present invention also relates to the non-therapeutic use of a polymer-cargo-complex of the invention for transfection. The term “transfection” means the process of deliberately introducing nucleic acids into eukaryotic cells, in particular in cell culture. The non-therapeutic use of the present invention includes both stable transfection and transient transfection. Stable and transient transfection differ in their long term effects on a cell; a stably-transfected cell will continuously express transfected DNA and pass it on to daughter cells, while a transiently-transfected cell will usually express transfected DNA for a short amount of time and not pass it on to daughter cells. RNA can also be transfected into cells to transiently express its coded protein, or to study RNA decay kinetics. RNA transfection is often used in primary cells that do not divide. siRNAs can also be transfected to achieve RNA silencing (i.e. loss of RNA and protein from the targeted gene). This has become a major application in research to achieve “knock-down” of proteins of interests with potential applications in gene therapy. However, the non-therapeutic use of the invention, although including transfection of siRNAs does not extend to applications in gene therapy and does in fact not include any treatment of the human or animal body by surgery or therapy nor diagnostic methods practiced on the human or animal body, Nucleic acids for non-therapeutic transfection are preferably selected from the group consisting of oligonucleotides and polynucleotides of DNA and/or RNA, in particular to mRNA, plasmids, self-amplifying RNAs, CRISPR/Cas systems, antisense oligo nucleotides, siRNA, miRNA and combinations of two or more thereof. In some embodiments, nucleic acids are selected from the group consisting of mRNA, siRNA and combinations thereof.

The present invention also relates to a non-therapeutic transfection method comprising the steps of Providing a polymer-cargo-complex of the invention, Incubating cells together with the polymer-cargo-complex.

The present invention also relates to a polymer-cargo-complex of the invention for use in therapy, in particular for use in gene therapy and/or delivery of peptide drugs, such as protein drugs. The present invention also relates to a polymer-cargo-complex of the invention for use in treatment of eye-related disorders, infections, cancers, cardiovascular diseases, asthma, hemophilia, renal failure, leukemia, and/or diabetes.

Nucleic acids are particularly interesting as antiviral actives since the viral nucleotides are easier to be selectively targeted than the rather few highly specific viral proteins. As consequence quite several antivirals are nucleoside analogs or molecules identified by genomics (antisense, ribozymes). Full potential of nucleic acids is only unraveled by potent delivery into infected mammalian cells, which is currently still hampered by toxicity of the used delivery systems.

Neuraminidase (NA) is an enzyme cleaving amino-glycoproteins chains at the glyosidic linkage of neuraminic acid. They are expressed by several pathogens (viruses, bacteria, parasitic protozoa, fungi) but also in mammalian cells. NA is the second important surface antigen of influenza viruses aside of Hemagglutinin (HA). Inhibition of viral neuraminidase interferes with the release of virions or the mammalian host cell and thus of virion spread. There are currently four NA inhibitors approved as influenza antivirals (Oseltamivir, Zanamivir, Peramivir and Inavir). While in general the susceptibility of influenza virus to NA inhibitors is good, the treatment needs to start early in infection for good therapeutic results. Importantly, more recently some alarming clusters of resistant influenza A were detected in Japan, China and the US. Strategies to prevent influenza infections as well as further treatment options are therefore an urgent medical need. In vaccination strategies the immunodominant HA was paid most attention to, since it is causing most protective antibodies. The high genetic instability of HA is the reason for the need of seasonal adaptation of the influenza vaccines. NA in contrast has less variants and a slower pace of mutagenesis. Antibody and T-lymphocyte mediated responses against NA are according to historic and recent results interesting ways leading to more universal influenza vaccination.

The polymer-cargo-complex of the present invention is a potent tool for using the immunogenic effect of Neuraminidase in single or combined vaccination. The excellent biocompatibility and degradation of the copolymer is a clear advantage against prior art strategies for preventive treatment like vaccination against infectious diseases.

Furthermore, the polymer-cargo-complex of the invention maximizes the delivery and transfection efficacy for transgenes by mRNA transfection. The transfection of relevant antigen presenting cells with neuraminidase may be tested in vitro (non-therapeutic use). Virus budding inhibition in vitro can be assessed (non-therapeutic use). In vivo studies may also test the immune response of the vaccination approach (therapeutic use).

As a further approach hitting the same target in therapeutic or acute preventive scenario (e.g. preventing spread in hospital-acquired infection), is an antisense strategy against the influenza neuraminidase by delivery using the polymer-cargo-complexes of the invention.

Coronavirus disease 2019 (COVID-19) caused by severe acute respiratory syndrome coronavirus 2 (SARS-CoV-2) is another viral disease that may be targeted by an antisense strategy using the polymer-cargo-complexes of the invention. In particular, entry receptors such as ACE2 and CD147 or the activating protease TMPRSS2 can be interfered with by inhibitory nucleotides delivered by the polymer-cargo-complexes of the invention.

The present invention also relates to the polymer-cargo-complex of the invention for use in treatment and/or prevention of viral diseases, in particular for use in treatment and/or prevention of influenza and/or COVID-19.

The present invention also relates to the polymer-cargo-complex of the invention for use as a vaccine, in particular against one or more of viral diseases, infections and cancers. In some embodiments, the invention relates to the polymer-cargo-complex of the invention for use as a vaccine against influenza and/or COVID-19, in particular against COVID-19. The low toxicity and high transfection efficiency of the polymer-cargo-complex of the invention makes them an ideal tool for delivering mRNA into the cells of interest. In some embodiments, the polymer-cargo-complex of the invention for use as a vaccine comprise mRNA as cargo molecule.

The present invention also relates to a therapeutic method such as gene therapy, in particular treatment and/or prevention of viral diseases, such as treatment and/or prevention of influenza and/or COVID-19. The method preferably comprises administering a polymer-cargo-complexes of the invention to a patient in need thereof. Preferably, the cargo molecules are nucleic acids. The present invention also relates to a method of vaccination against one or more of viral diseases, infections and cancers, the method comprising administering a polymer-cargo-complex of the invention. In some embodiments, the invention relates to a method of vaccination against influenza and/or COVID-19, in particular against COVID-19. The polymer-cargo-complex of the invention may for example be administered subcutaneously or intramuscularly.

The present invention also relates to a kit comprising a polymer-cargo-complex of the invention and instructions for use thereof. Such a kit may for example be a kit for non-therapeutic transfection of eukaryotic cells, in particular in cell culture, or a kit for gene therapy, for example for vaccination.

The present invention also relates to a method of preparing a polymer-cargo-complex of the invention, the method comprising the following steps:

a) Providing an aqueous solution comprising (i) hydrazides of amino acids and (ii) dialdehydes comprising a polyethylene glycol (PEG) group, preferably carbazole dicarboxaldehydes comprising a PEG group, wherein the solution has a pH in the range of from 2 to 6, and wherein 40 to 100 mol %, for example 50 to 99.9 mol %, 60 to 99 mol %, 70 to 98 mol %, 80 to 95 mol %, or 85 to 90 mol % of the hydrazides are hydrazides of either cationic amino acids selected from the group consisting of lysine, arginine, histidine and combinations of two or more thereof, or anionic amino acids selected from the group consisting of aspartic acid, glutamic acid and combinations thereof,
b) Incubating the solution to allow copolymer formation,
c) Mixing the formed copolymer with a cargo molecule in an aqueous solution,
d) Forming a cross-linked copolymer, optionally by adding amino acid side chain-specific cross-linker to the solution,
e) Increase the pH of the solution to at least 7.

The method may comprise an additional step f) of purifying the cross-linked copolymer. Such a purification step is optional.

Preferably, 40 to 100 mol %, for example 50 to 99.9 mol %, 60 to 99 mol %, 70 to 98 mol %, 80 to 95 mol %, or 85 to 90 mol % of the hydrazides are hydrazides of cationic amino acids selected from the group consisting of lysine, arginine, histidine and combinations of two or more thereof.

Preferably, 0 to 60 mol %, for example 0.1 to 50 mol %, 1 to 40 mol %, 2 to 30 mol %, 5 to 20 mol %, or 10 to 15 mol % of the hydrazides are hydrazides of amino acids selected from the group consisting of serine (Ser), threonine (Thr), asparagine (Asn), glutamine (Gln), cysteine (Cys), glycine (Gly), proline (Pro), alanine (Ala), valine (Val), isoleucine (Ile), leucine (Leu), methionine (Met), phenylalanine (Phe), tyrosine (Tyr), tryptophan (Trp) and combinations of two or more thereof.

In step a) of the method of the invention, the pH of the aqueous solution is kept in a range of from 2 to 6, for example from 2.5 to 5.5, from 3.0 to 5.0, or from 3.5 to 4.5. This enables efficient polymer formation based on reaction of the hydrazides of amino acids and the dialdehydes, in particular the carbazole dicarboxaldehydes. In particular, formation of acylhydrazone groups and imine groups requires acidic pH values. Preferably, pH of the aqueous solution of step a) is achieved with acetate buffer or with HCl. Preferably, the concentration of both the hydrazides of amino acids and the dialdehydes comprising a PEG group is in a range of from 1 mM to 100 mM, more preferably from 2 mM to 50 mM, more preferably from 5 mM to 20 mM. Preferably, the ratio of the concentration of the hydrazides of amino acids to the concentration of the dialdehydes comprising a PEG group is in a range of from 0.1:1 to 10:1, more preferably from 0.2:1 to 5:1, more preferably from 0.5:1 to 2:1, more preferably from 0.8:1 to 1.2:1, more preferably from 0.9:1 to 1.1:1, more preferably about 1:1.

Step b) is an incubation step to allow copolymer formation. Notably, the monomers polymerize in acidic aqueous solution without any additional reagent. The incubation time is preferably from 6 to 96 hours, such as from 12 to 72 hours or from 24 to 48 hours, at a temperature of preferably from 4 to 60° C., such as from 15 to 40° C. or from 20 to 30° C.

In step c), the formed copolymer is mixed with a cargo molecule in an aqueous solution. This may be done by adding the cargo molecule into the solution of steps a) and b). However, the method may comprise an additional step b2) of preparing an aqueous solution of the formed copolymer with reduced ionic strength (in particular an ionic strength in a range of from 0 to 20 mM, preferably from 1 to 10 mM), wherein step b2) is done after step b) but prior to step c).

Step b2) may comprise diluting the aqueous solution of steps a) and b) with a low ionic strength solution such as for example water, in particular deionized water. The term "deionized water" (also referred to as "DI water") refers to water that has had its mineral ions removed, such as cations like sodium, calcium, iron, and copper, and anions such as chloride and sulfate. The dilution step may include a dilution of from 5-fold to 100-fold, for example 10-fold to 50-fold or 20-fold to 40-fold, as compared to the aqueous solution of steps a) and b). Additionally or alternatively, step b2) may comprise lyophilization (freeze-drying) of the formed copolymer and re-dissolving the freeze-dried copolymer in an aqueous solution having low ionic strength such as for example 1 mM acetate buffer. Preferably, the concentration of the formed copolymer in the aqueous solution obtained by step b2) is in a range of from 10 μg/ml to 500 μg/ml, more preferably from 25 μg/ml to 400 μg/ml, more preferably from 50 μg/ml to 350 μg/ml, more preferably from 100 μg/ml to 300 μg/ml, more preferably from 150 μg/ml to 250 μg/ml.

Step c) of mixing the formed copolymer with a cargo molecule in an aqueous solution may be done by adding the cargo molecule to the solution obtained by step b2).

Preferably, the aqueous solution of step c) has a pH in a range of from 2.0 to 6.0, for example from 2.5 to 5.5, from 3.0 to 5.0, or from 3.5 to 4.5.

Preferably, the cargo molecules added in step c) are nucleotides. Preferably, the cargo molecules, in particular the nucleotides, are added such that the NP ratio is from 1 to 50, for example from 2 to 40, from 5 to 30 or from 10 to 20.

In step c) a complex is formed between the copolymer and the cargo molecules.

In particular, the cargo molecules bind to the copolymer by electrostatic interactions between the cargo molecules and the amino acid side chains of the copolymer.

In step d) of the method optionally an amino acid side chain-specific cross-linker is added to the solution. The amino acid side chain-specific cross-linker is introducing a cross-linking group linking together two amino acid side chains. Generally, there is a great variety of amino acid side chain-specific cross-linkers. In particular, cross-linkers may be different depending on the amino acid side chains that are cross-linked. Preferably, the amino acid side chain-specific cross-linker is selected from the group consisting of amine-specific cross-linkers and cross-linkers comprising electrophilic reactive groups. Amine-specific cross-linkers are particularly advantageous for cross-linking lysine, arginine and/or histidine side chains. Cross-linkers comprising electrophilic reactive groups are particularly advantageous for cross-linking nucleophilic amino acid side chains, in particular side chains of lysine, cysteine, serine, threonine and/or tyrosine.

Amine-specific cross-linking may for example include covalent bonds formed between primary amines and cross-linkers containing isothiocyanates, isocyanates, acyl azides, NHS (N-hydroxysuccinimide) esters, sulfonyl chlorides, aldehydes, glyoxals, epoxides, oxiranes, carbonates, aryl halides, imidoesters, carbodiimides, anhydrides, fluorophenyl esters and combinations of two or more thereof. Preferably, the amino acid side chain-specific cross-linker is selected from the group consisting of aldehydes, isothiocyanates, isocyanates, acyl azides, NHS esters, sulfonyl chlorides, glyoxals, epoxides, oxiranes, carbonates, aryl halides, imidoesters, carbodiimides (for example EDC (1-Ethyl-3-(3-dimethylaminopropyl)carbodiimide)), anhydrides, fluorophenyl esters (in particular pentafluorophenyl esters), hydroxymethyl phosphines and combinations of two or more thereof. Preferably, the amine-specific cross-linker is an aldehyde, in particular glutaraldehyde. Particularly preferred, the amino acid side chain-specific crosslinker is an amine-specific cross-linker and the amine-specific cross-linker is an aldehyde, in particular glutaraldehyde.

Preferably, the cross-linker comprising electrophilic reactive groups is selected from the group consisting of maleimide, haloacetyl (bromo- or iodo-), pyridyldisulfide, thiosulfonate, vinylsulfone and combinations of two or more thereof.

Preferably, the amino acid side chain-specific cross-linker is selected from the group consisting of aldehydes (preferably glutaraldehyde), isothiocyanates, isocyanates, acyl azides, NHS esters, sulfonyl chlorides, glyoxals, epoxides, oxiranes, carbonates, aryl halides, imidoesters, carbodiimides (for example EDC (1-Ethyl-3-(3-dimethylaminopropyl) carbodiimide)), anhydrides, fluorophenyl esters (in particular pentafluorophenyl esters), hydroxymethyl phosphines, maleimide, haloacetyl (Bromo- or Iodo-), pyridyldisulfide, thiosulfonate, vinylsulfone and combinations of two or more thereof.

Preferably, the amino acid side chain-specific cross-linker is added in step d) such that the resulting concentration of the cross-linker is in a range of from 1 to 100 wt.-%, more preferably from 5 to 100 wt.-%, more preferably from 10 wt.-% to 100 wt. %, for example from 10 wt.-% to 50.-%, from 15 wt.-% to 40 wt.-%, or from 20 wt.-% to 30 wt.-% as compared to the concentration of copolymer. In some embodiments, the resulting concentration of the cross-linker may be in a range of from 15 wt.-% to 75 wt. %, for example from 20 wt.-% to 60 wt.-%, or from 25 wt.-% to 50 wt.-%. The resulting concentration of the cross-linker may for example be at least 1 wt.-%, at least 5 wt.-%, at least 10 wt.-%, at least 15 wt.-%, at least 20 wt.-%, or at least 25 wt.-%. The resulting concentration of the cross-linker may for example be at most 100 wt.-%, at most 75 wt. %, at most 60 wt.-%, at most 50 wt.-%, at most 40 wt.-%, or at most 30 wt.-%.

Step d) of adding an amino acid side chain-specific cross-linker to the solution is an optional step of the method of the invention. Alternatively or in addition to chemical cross-linking by adding an amino acid side chain-specific cross-linker to the solution, physical cross-linking can be used, in particular cross-linking by hydrophobic interactions, electrostatic interactions, salt-bridge, host-guest interactions, hydrogen bonds between the amino acid side chains or combinations of two or more thereof.

In step e), the pH of the solution is increased to at least 7. This is advantageous for further stabilizing the polymer-cargo-complexes of the invention. Preferably, the pH is increased by adding buffer, preferably HBSS (Hank's Balanced Salt Solution). Drastic pH changes are preferably avoided. Preferably, the pH is increased in step e) to a pH value of at most 8.

Subsequently, the volume of the solution may be adjusted, for example using HBSS buffer.

Preferably, the zeta potential of the copolymer and the zeta potential of the cargo molecule have opposite signs (the zeta potential of the copolymer being positive and the zeta potential of the cargo molecule being negative or the zeta potential of the copolymer being negative and the zeta potential of the cargo molecule being positive).

Preferably, the sum of the absolute values of the zeta potential of the copolymer and the zeta potential of the cargo molecule is at least 10 mV. Preferably, the sum of the absolute values of the zeta potential of the copolymer and the zeta potential of the cargo molecule is in a range of from 10 mV to 75 mV, more preferably from 15 mV to 50 mV, more preferably from 20 mV to 35 mV. Preferably, the zeta potential is determined using electrophoretic light scattering (for example using Zetasizer (in particular Zetasizer Nano ZSP, Malvern Panalytical, United Kingdom)) at a concentration of 2 mg/mL in 50 mM acetate buffer at pH 5.0, in particular at a temperature of 25° C.

The present invention also relates to a kit for preparing a polymer-cargo-complex of the invention, the kit comprising amino acid hydrazides and dialdehydes comprising a PEG group, in particular carbazole dicarboxaldehydes comprising a PEG group. Optionally, the kit may further comprise amino acid side chain-specific cross-linker. The kit may also comprise DI water and/or buffers. Preferably, the kit comprises instructions for use. The kit may also comprise cargo molecules. However, the kit is also enabling preparation of polymer-cargo-complexes with cargo molecules of interest provided by the customer. Preferably, the kit comprises hydrazides of basic amino acids if the cargo molecule of interest has negative zeta potential. Likewise, the kit preferably comprises hydrazides of acidic amino acids if the cargo molecule of interest has positive zeta potential. The kit may also comprise hydrazides of lysine (Lys), arginine (Arg), histidine (His), aspartic acid (Asp), and glutamic acid (Glu) and optionally also hydrazides of serine (Ser), threonine (Thr), asparagine (Asn), glutamine (Gin), cysteine (Cys), glycine (Gly), proline (Pro), alanine (Ala), valine (Val), isoleucine (Ile), leucine (Leu), methionine (Met), phenylalanine (Phe), tyrosine (Tyr) and tryptophan (Trp). Preferably, the kit comprises each chemical compound in a separate container. Preferably, the kit also comprises instructions for use.

The copolymer concentration is shown on the x-axis. The results are shown for two different pH conditions.

Figure 2:
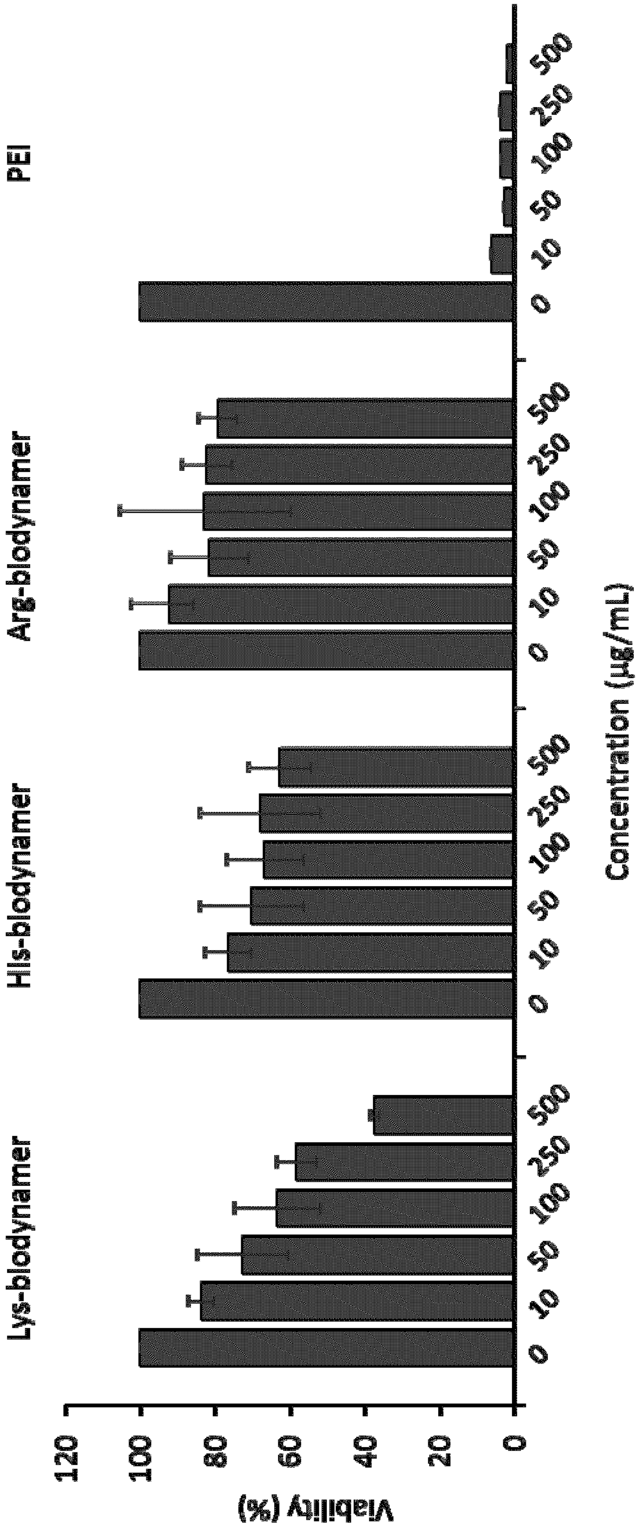

FIG. 2 is a bar graph showing cell viability in presence of different concentrations of copolymers. In addition to Lys-biodynamers, biodynamers obtained from His-hydrazide and $PEG_6$ylated carbazole dicarboxaldehyde (His-biodynamers) and from Arg-hydrazide and $PEG_6$ylated carbazole dicarboxaldehyde (Arg-biodynamers) have been tested as well. Prior art compound PEI was used as a control. The copolymers of the invention have strongly reduced cytotoxicity as compared to the prior art, Cytotoxicity was tested in A549 cells using the MTT (3-(4,5-dimethylthiazol-2-yl)-2, 5-diphenyltetrazolium bromide) assay.

Figure 3:
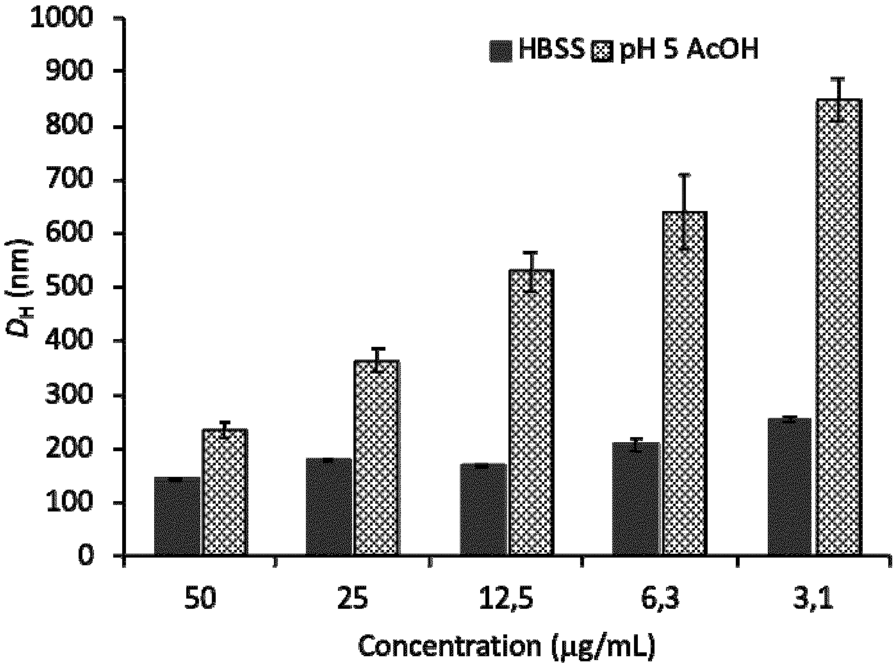

FIG. 3 is a bar graph showing the hydrodynamic diameter $D_H$ of a polymer-cargo-complex nanoparticle formed by electrostatic interaction of the Lys-biodynamer with mCherry mRNA. The y-axis shows the average $D_H$ (±standard deviation) determined by DLS. The nanoparticle concentration is shown on the x-axis. The results are shown for two different pH conditions (pH 5.0 (AcOH) and pH 7.4 (HBSS), respectively).

Figure 4:
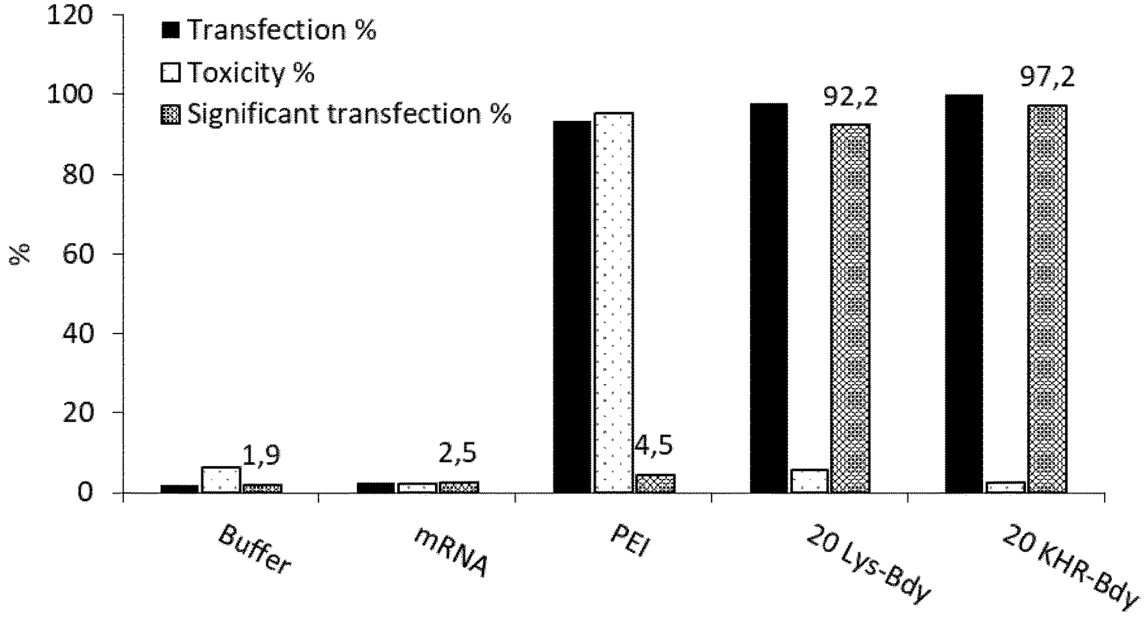

FIG. 4 shows transfection efficiency (of mCherry mRNA) and toxicity of PEI and polymer-cargo-complexes of the present invention. A549 cells were incubated for 2 hours with different transfection reagents (present invention and prior art). Subsequently, the cells were washed and further incubated for 24 hours in a cell culture medium for protein expression, then followed by flow cytometry measurement for evaluation of transfection efficiency and cell viability. Transfection efficiency was assessed by mCherry fluorescence. Cell viability was assessed using an amine reactive dye (DAPI (4',6-diamidine-2'-phenylindole dihydrochloride)) resulting in weakly stained non-permeable live cells and more highly fluorescent dead cells due to increased permeability of the membranes. Buffer and mRNA without transfection agents were used as negative controls. Significant transfection was calculated by multiplying the percentage of transfected cells with the percentage of viable cells. The significant transfection using polymer-cargo-complexes of the present invention is about 20 times higher as compared to prior art PEI.

Figure 5:
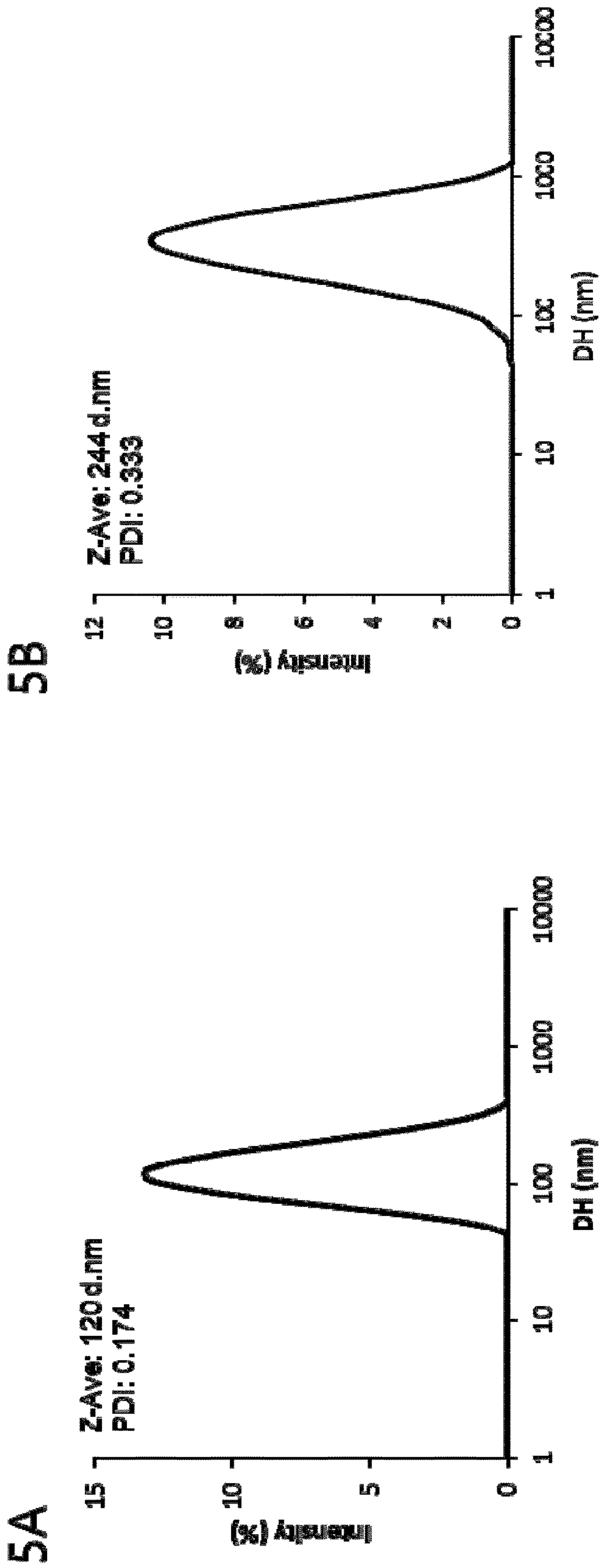

FIG. 5 shows DLS data showing the size distribution of polymer-cargo-complexes of the invention. The x-axis depicts the hydrodynamic diameter $D_H$ of the polymer-cargo-complexes (in nrm) on a logarithmic scale. The y-axis depicts the intensity (in %). FIG. 5A shows the results of polymer-cargo-complexes having mCherry mRNA as model nucleic acid cargo molecule. The Z-average hydrodynamic diameter was determined to be 120 nm. The polydispersity index (PDI) was 0.174. FIG. 5B shows the results of polymer-cargo-complexes having albumin-fluorescein isothiocyanate conjugate as model peptide cargo molecule. The Z-average hydrodynamic diameter was determined to be 244 nm. The polydispersity index (PDI) was 0.333.

Figure 6:
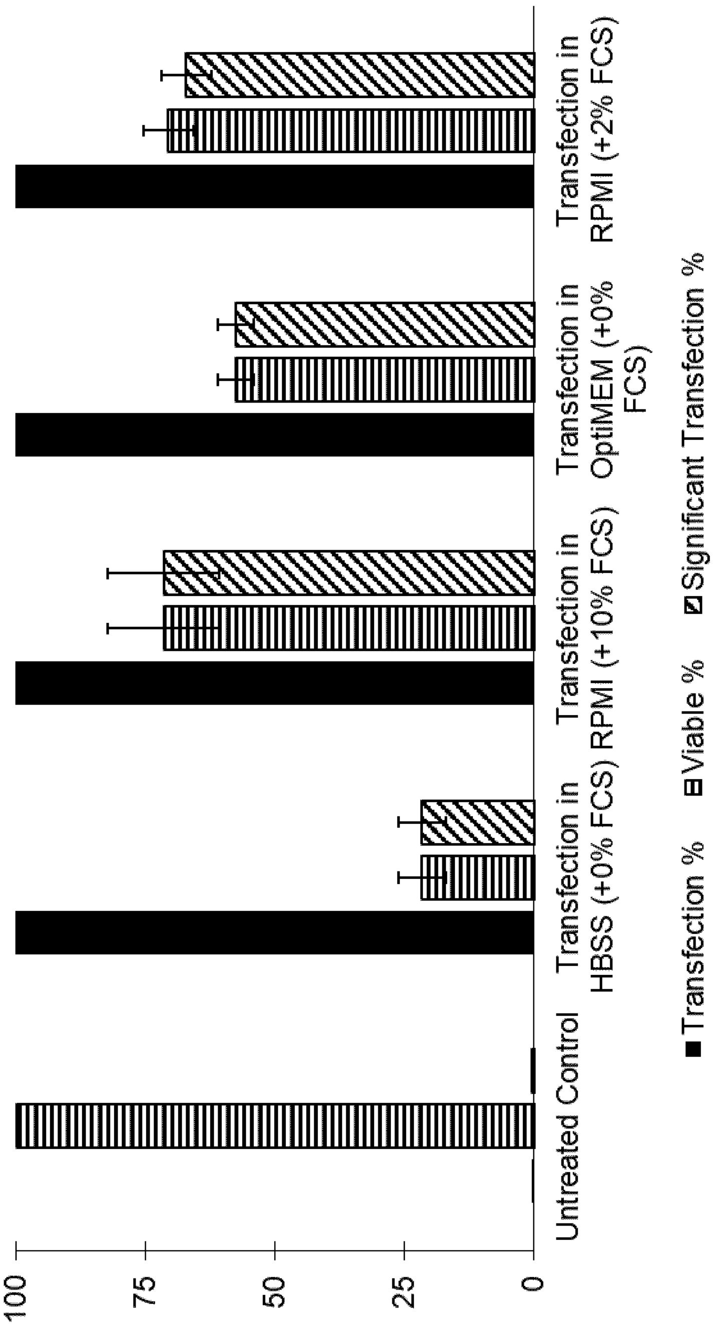

FIG. 6 shows transfection efficiency (of mCherry mRNA) and toxicity of polymer-cargo-complexes of the present invention. As polymer-cargo-complexes, mCherry encoding mRNA complexed with KHR-BDy was used. DC2.4 cells were incubated for 2 hours with the polymer-cargo-complexes in various cell culture medium conditions as indicated in FIG. 6. Subsequently, the cells were washed and further incubated for 24 hours in the indicated cell culture medium conditions for protein expression, then followed by flow cytometry measurement for evaluation of transfection efficiency and cell viability. Transfection efficiency was assessed by mCherry fluorescence. Cell viability was assessed using an amine reactive dye (DAPI (4'6-diamidine-2'-phenylindole dihydrochloride)) resulting in weakly stained non-permeable live cells and more highly fluorescent dead cells due to increased permeability of the membranes. Untreated cells were used as control. Significant transfection was calculated by multiplying the percentage of transfected cells with the percentage of viable cells. The y-axis shows the results for the different conditions (±standard deviation).

Figure 7:
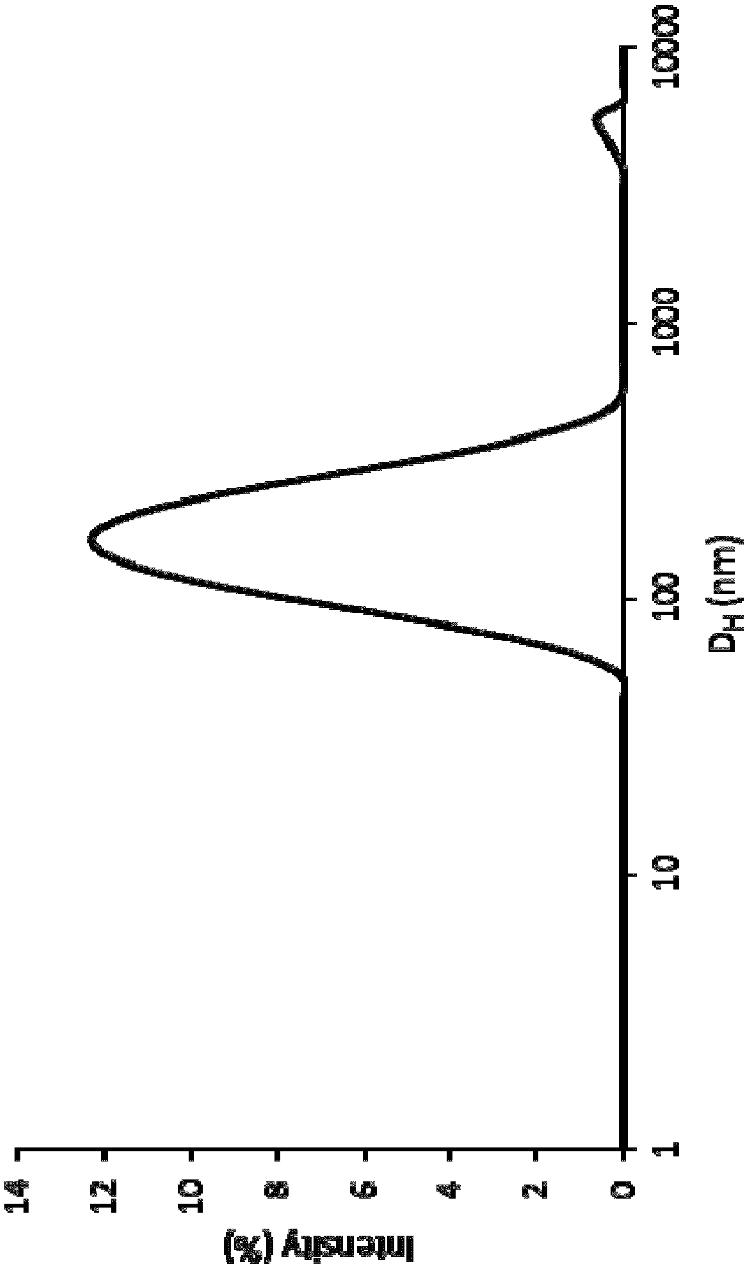

FIG. 7 shows DLS data showing the size distribution of polymer-cargo-complexes of the invention. The x-axis depicts the hydrodynamic diameter $D_H$ of the polymer-cargo-complexes (in nm) on a logarithmic scale. The y-axis depicts the scattering intensity (in %). FIG. 7 shows the results of polymer-cargo-complexes ($D_H$=126 nm, PDI=0.321) of positively charged Arg-Phe-biodynamer (RF-biodynamer) with negatively charged insulin as cargo molecule.

Figure 8:
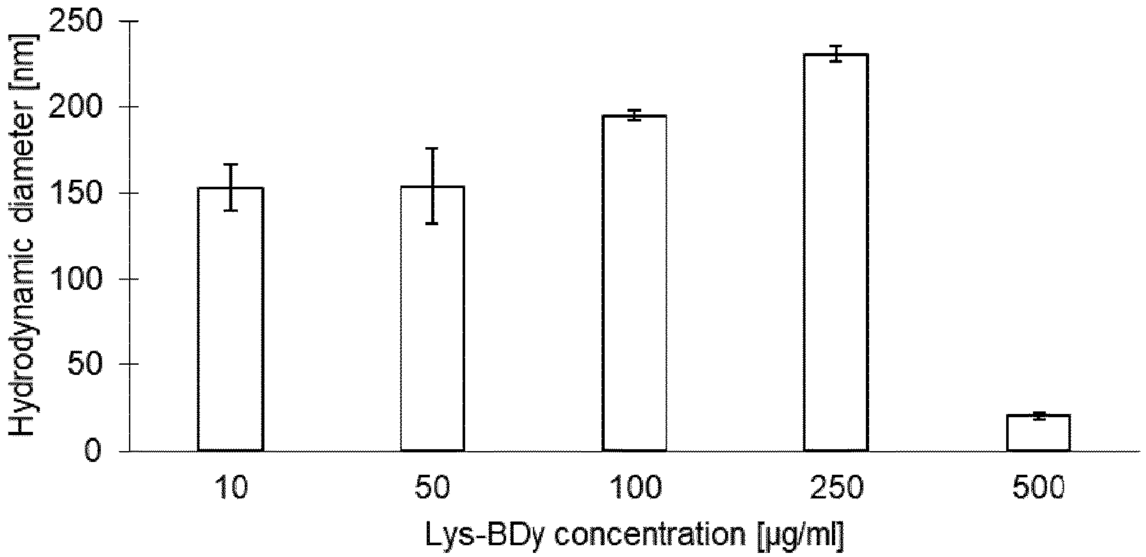
Figure 8:
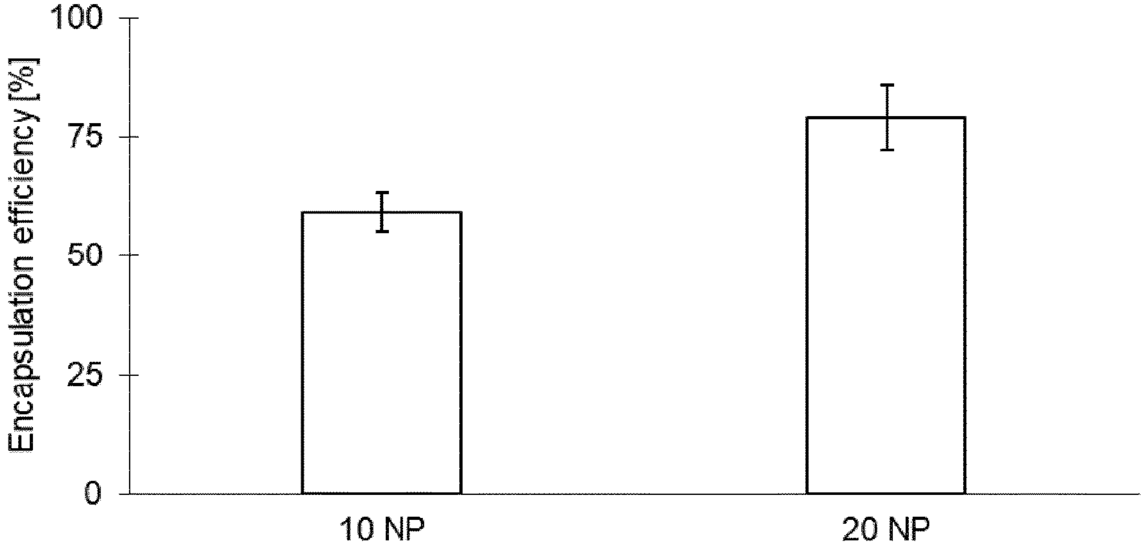

FIG. 8 summarizes properties of polymer-cargo-complexes formed from Lys-biodynamer and a model siRNA, alexa-594-conjugated siRNA. FIG. 8A is a bar graph showing the hydrodynamic diameter $D_H$ of a polymer-cargo-complex nanoparticle formed by electrostatic interaction of the Lys-biodynamer with alexa-594-conjugated siRNA. The y-axis shows the average $D_H$ (±standard deviation) determined by DLS. The nanoparticle concentration is shown on the x-axis. FIG. 8B is a bar graph showing the encapsulation efficiency (in % (w/w)) for two different NP ratios (±standard deviation).

Figure 9:
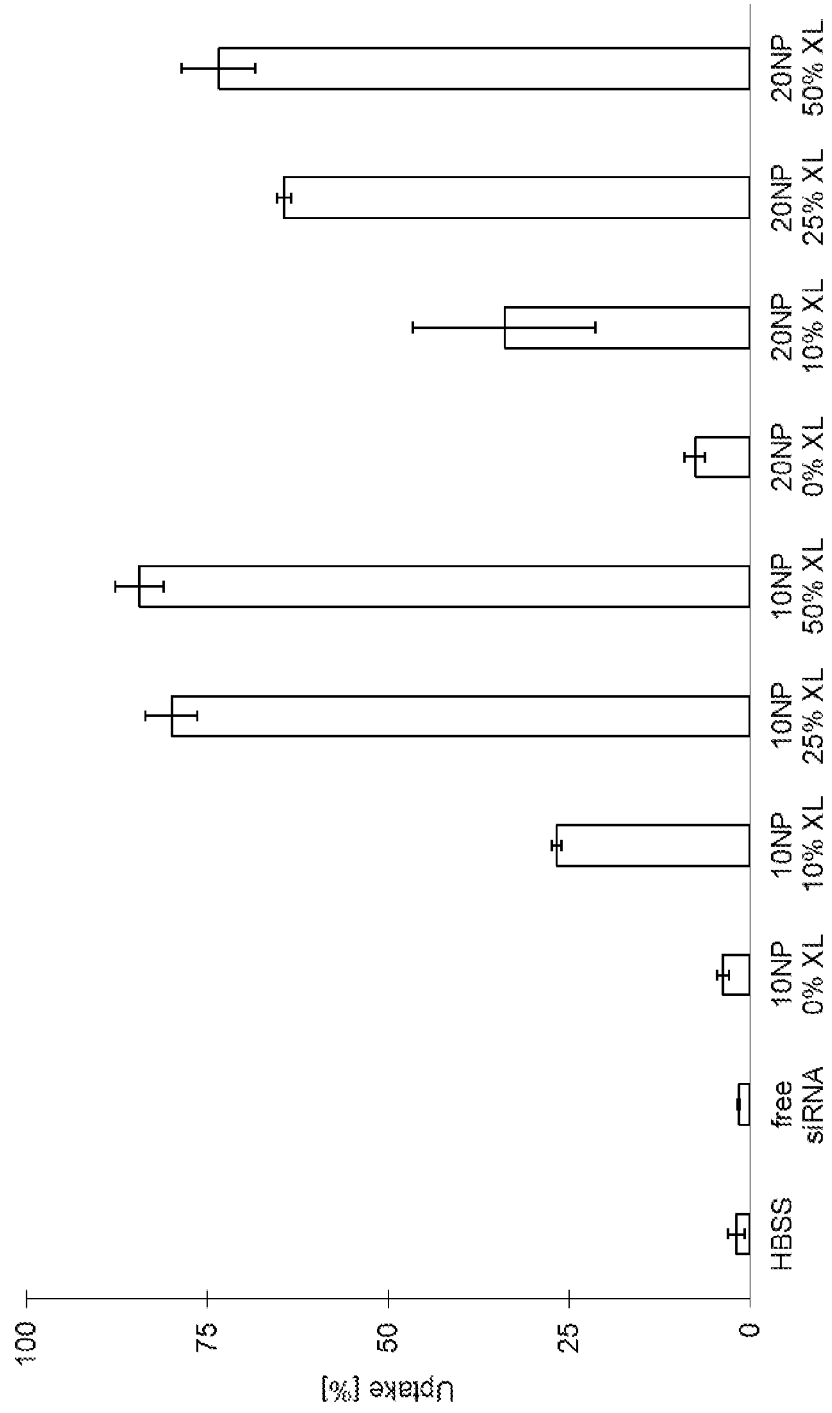

FIG. 9 shows cellular uptake of the polymer-cargo-complexes formed from Lys-biodynamer and Alexa594-labelled siRNA. A549 cells were incubated for 2 hours with different transfection reagents (present invention and prior art). Cellular uptake was assessed by fluorescence-activated cell sorting. HBSS buffer and free siRNA without copolymer of the invention were used as negative controls. The y-axis shows the cellular uptake (±standard deviation).

EXAMPLES

Preparation of the Copolymer

General Methods and Instrumentation

All reagents were obtained from commercial suppliers without further purification.

Procedures were not optimized regarding yield. NMR spectra were recorded on a Bruker AV 500 (500 MHz) spectrometer. Liquid chromatography-Mass spectrometry was performed on a SpectraSystems-MSQ LCMS system (Thermo Fisher, Dreieich, Germany). Flash chromatography was performed using the automated flash chromatography system CombiFlash Rf+ (Teledyne Isco, Lincoln, NE, USA) equipped with RediSepRf silica columns (Axel Semrau, Sprockhövel Germany) or Chromabond Flash C18 columns (Macherey-Nagel, Düren, Germany). The purity of compounds synthesized by us was determined by LC-MS using the area percentage method on the UV trace recorded at a wavelength of 254 nm and found to be >95%.

Synthesis

The following scheme is an overall synthesis scheme of a particular preferred copolymer.

Synthesis of Compound b1

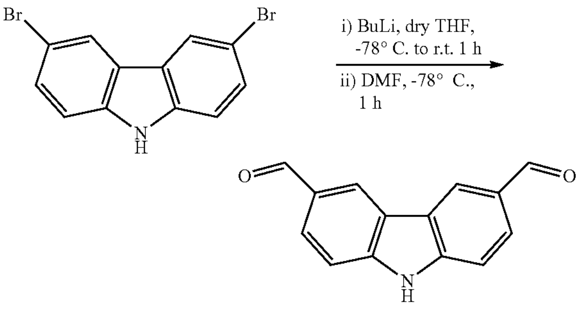

b1

Carbazole dialdehyde (b1) was prepared according to a literature procedure (J. F. Folmer-Andersen, E. Buhler, S.-J. Candau, S. Joulie, M. Schmutz, J.-M. Lehn, *Polym. Int.* 2010, 59, 1477 and D. A. Patrick, D. W. Boykin, W. D Wilson, F. A. Tanious, J. Spychala, B. C. Bender, J. E. Hall,

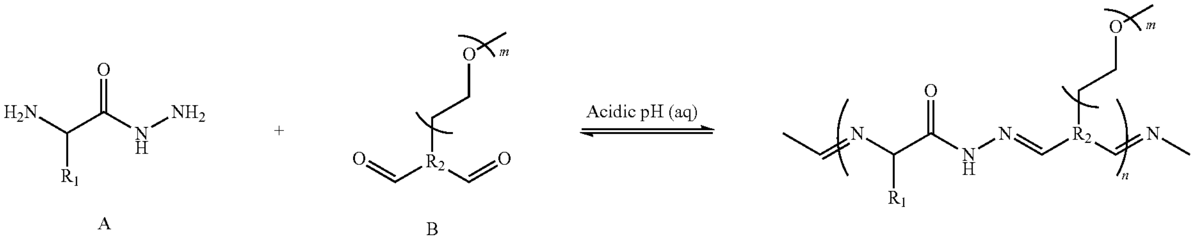

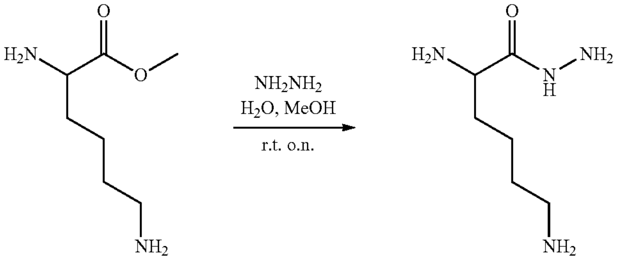

A1

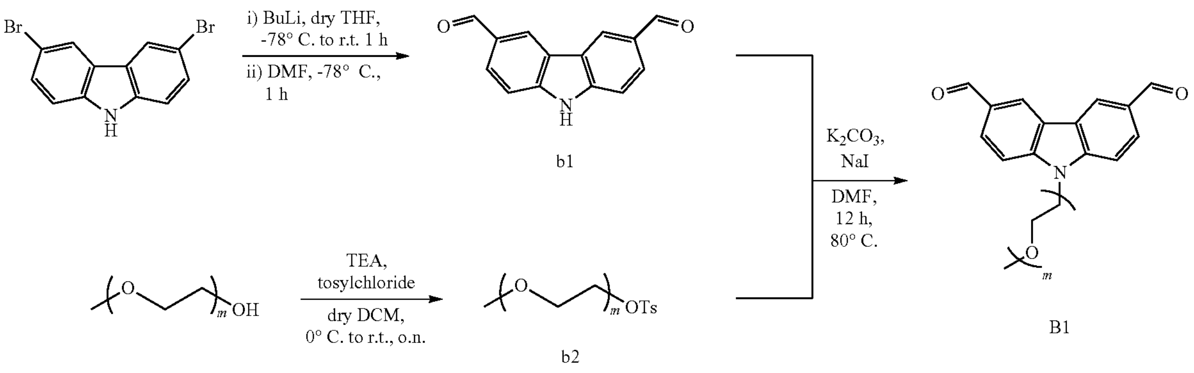

In the following, the different synthesis steps are described in more detail.

C. C. Dykstra, K. A. Ohemeng, R. R. Tidwell, *Eur. J. Med. Chem.* 1997, 32, 781-793). Briefly, 3,6-dibromocarbazole (3.02 g, 9.29 mmol) was dissolved in anhydrous tetrahydrofuran (THF, 60 ml) to give a pale brown solution. The solution was set stirring in a dry ice/acetone bath. An amount of 26 mL of a solution of n-butyllithium (n-BuLi) (2.5 mM in hexane, 65.03 mmol) was then added over a period of 10-15 minutes, causing the reaction contents to become light yellow. The cooling bath was removed for 1 h and then replaced back. After 10 min, anhydrous dimethylformamide (DMF, 7.55 mi, 97.54 mmol) was added over 10 min, causing the precipitation of a pale yellow solid. The cooling bath was removed and the reaction was stirred for 90 more minutes. After this, it was quenched with 1 M hydrochloric acid (HCl) solution and the reaction was suction filtered. The filtrate was extracted with ethylacetate (EtOAc, 5×50 ml) and the combined organic layers were washed with brine, dried over anhydrous sodium sulface ($Na_2SO_4$). The orange oily product was purified via combiflash column chromatography (dichloromethane (DCM):methanol 97:3) yielding 260 mg (15%) off-white solid. $^1$H-NMR is in agreement with those previously reported (J. F. Folmer-Andersen, E. Buhler, S.-J. Candau, S. Joulie, M. Schmutz, J.-M. Lehn, *Polym. Int.* 2010, 59, 1477 and D. A. Patrick, D. W. Boykin, W. D. Wilson, F. A. Tanious, J. Spychala, B. C. Bender, J. E. Hall, C. C. Dykstra, K. A. Ohemeng, R. R. Tidwell, *Eur. J. Med. Chem.* 1997, 32, 781-793).

Synthesis of compound B1

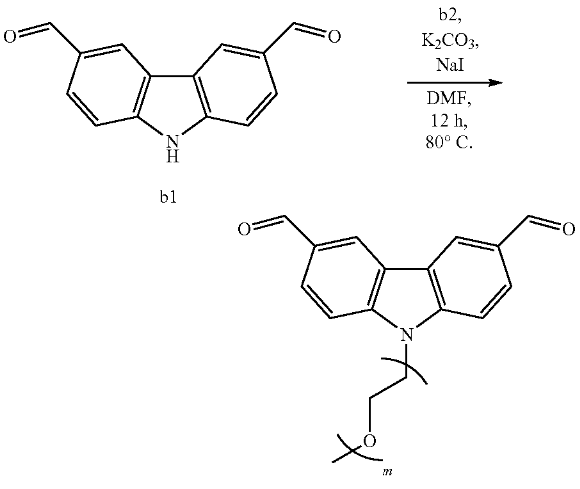

b1

B1

Compound b1 (1.27 g, 5.69 mmol) is dissolved in 70 ml of DMF. Tosylated hexaethylene glycol monometyl ether (compound b2, m is 6 in this example) prepared according to a literature procedure (J. F. Folmer-Andersen, E. Buhler, S-J. Candau, S. Joulie, M. Schmutz, J.-M. Lehn, *Polym. Int.* 2010, 59, 1477 and D. A. Patrick, D. W. Boykin, W. D. Wilson, F. A. Tanious, J. Spychala, B. C. Bender, J. E. Hall, C. C. Dykstra, K. A. Ohemeng, R. R. Tidwell, *Eur J. Med. Chem.* 1997, 32, 781-793) Compound b2 (2.50 mg, 5.55 mmol) was added to this solution followed by potassium carbonate ($K_2CO_3$, 2.54 g, 18.38 mmol). 10 mg of sodium iodide (NaI) is added to this mixture and the reaction was stirred at 80° C. to reflux overnight. Extraction was done with DCM and the organic phase was washed with brine. The compound was purified using flash chromatography with ethylacetate/$^i$propanol (5:1) 2.22 g product was obtained as a pale yellow liquid which occasionally solidified upon standing. (Yield 80%) The 1H-NMR of the product agreed with previous reports (J. F. Folmer-Andersen, E. Buhler, S-J. Candau, S. Joulie, M. Schmutz, J.-M. Lehn, *Polym. Int.* 2010, 59, 1477 and D. A. Patrick, D. W. Boykin, W. D. Wilson, F. A. Tanious, J. Spychala, B. C. Bender, J. E. Hall, C. C. Dykstra, K. A. Ohemeng, R. R. Tidwell, *Eur. J. Med. Chem.* 1997, 32, 781-793).

Synthesis of Compound A1

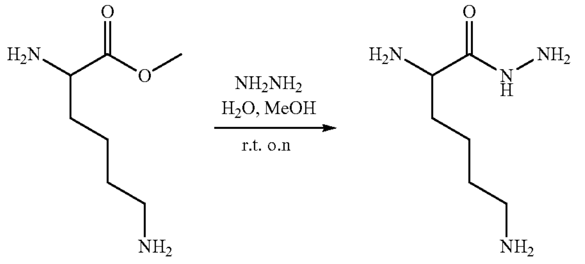

A1

Monomer A ($R_1$ is a side chain of lysine in this example, A1) is prepared according to a literature procedure (Y. Liu, M. C. A. Stuart, E. Buhler, J.-M. Lehn, A. K. H. Hirsch, *Adv. Funct. Mater.* 2016, 26, 6297). To a solution of the L-lysine methyl ester hydrochloride (750 mg, 3.2 mmol) in methanol (15 mL), hydrazine monohydride (25.8 mmol) was added. The reaction mixture was stirred at 25° C. for 20 h. The mixture was then concentrated and dried overnight in a high vacuum. After lyophilization, L-lysine hydrazide was obtained as liquid (495 mg, 96%) $^1$H-NMR is in agreement with those previously reported (Y. Liu, M. C. A. Stuart, E. Buhler, J.-M. Lehn, A. K. H. Hirsch, *Adv. Funct. Mater.* 2016, 26, 6297).

Synthesis of the Copolymer (Biodynamer) from Monomer A1 and B1

Each monomer was dissolved in 100 mM d-acetate buffer (pD 5.0) in a final concentration of 20 mM. The monomer solutions were mixed with a ratio of 50:50. After 24 hours of reaction at room temperature (r.t.), the resulting mixture was filtered using a 0.22 μm polyethersulfone (PES) syringe filter. Polymerization was confirmed by consumption of the aldehyde proton peaks, analyzed by $^1$H-NMR, and nanorod formation was observed by dynamic light scattering (DLS). $^1$H-NMR peaks of the biodynamer agreed with the previous report.

Formulation Scheme of the Polymer-Cargo-Complex

The resulting copolymers (biodynamers) in an acidic aqueous solution diluted to 100 μg/mL with deionized water. Nucleic acids or proteins were added to the biodynamer solution with a calculated amount based on the NP ratio or the zeta potential, respectively, and vortexed for 3 seconds. In particular, the copolymer (zeta potential=16.7 mV) was mixed with cargo having negative zeta potential (e.g. luciferase siRNA (2 mg/mL)=−7.99+−3.8 mV in 50 mM acetate buffer pH 5 or albumin (2 mg/mL albumin-fluorescein isothiocyanate conjugate, Merck, Germany)=−10.04+−0.82 mV in 50 mM acetate buffer pH 5). Regarding luciferase siRNA as cargo molecule, the amount as used was such that the NP ratio was 10:1. Regarding the peptide cargo molecule (albumin-fluorescein isothiocyanate conjugate), the amount as used was 5 wt.-% as compared to the amount of copolymer (biodynamer). Polymer-cargo-complexes were formed as nanoparticles. The formed nanoparticles (polymer-cargo-complexes) stabilized at r.t. for 1 hour before characterizations or uses.

Crosslinking Scheme

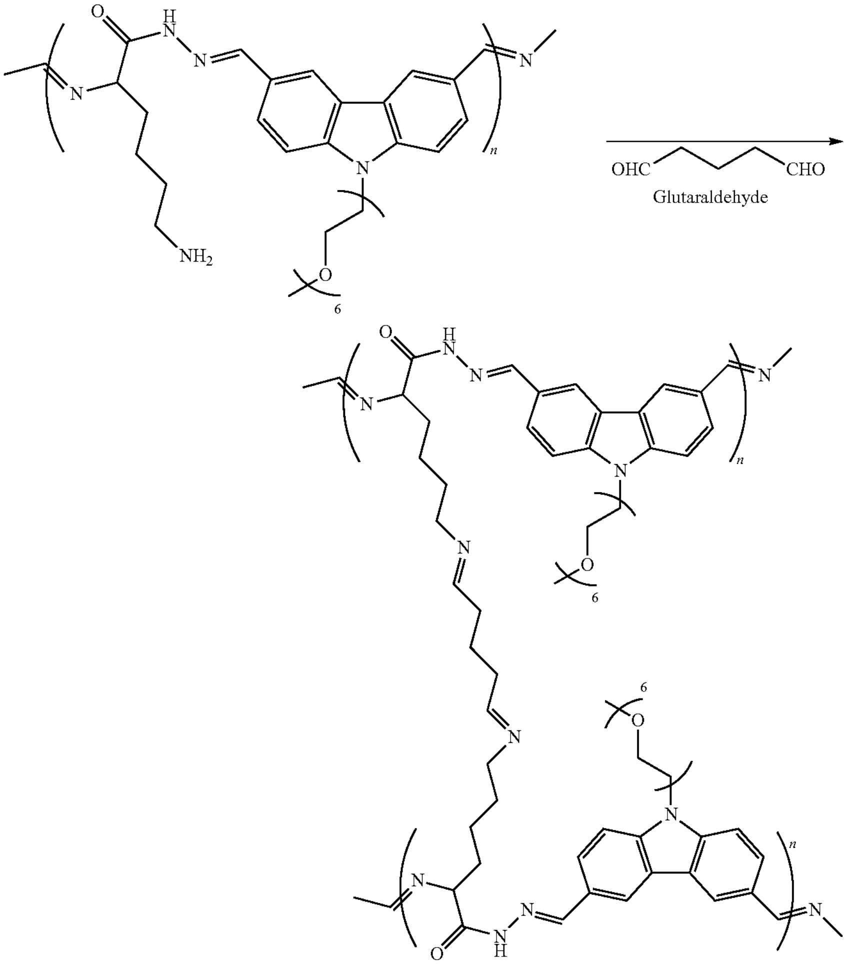

After the polymer-cargo-complex formulation, a crosslinking agent (e.g., glutaraldehyde) crosslinked amino acid side chains to improve particle stability. Glutaraldehyde solution (16%) was diluted 100 folds with deionized water. The diluted glutaraldehyde solutions were added into the nanoparticle solutions with μL scales. The exact amount of the glutaraldehyde was calculated based on the w % of the biodynamers. The resulting mixture was vortexed for a few seconds and stored at r.t. overnight.

Hydrodynamic Size of Nanoparticles

Copolymers were produced by the method of the invention using Lys-hydrazide (A1) and $PEG_6$ylated carbazole dicarboxaldehyde (B1) as described above.

Figure 1:
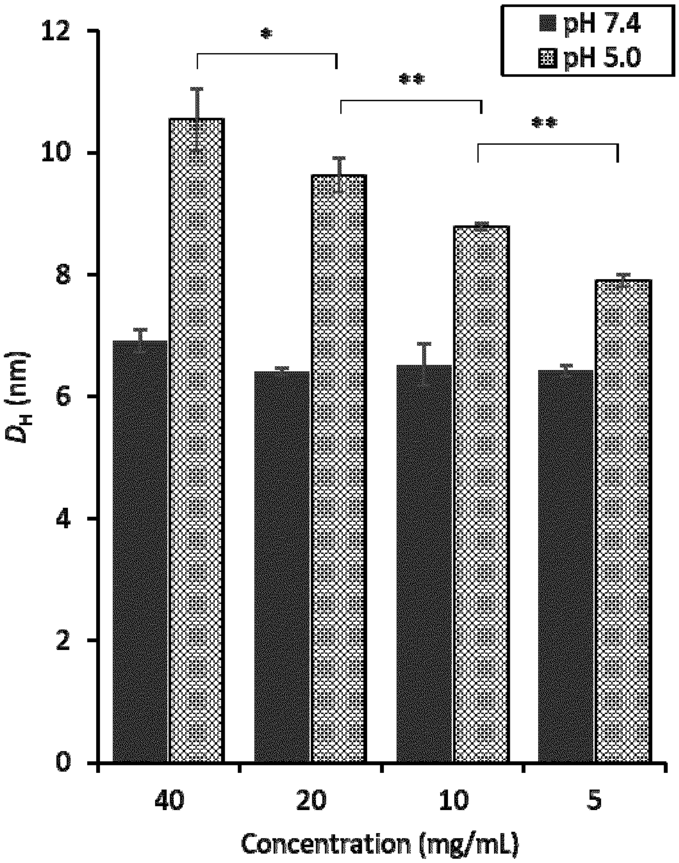
FIG. 1 is a bar graph showing the hydrodynamic diameter $D_H$ of a copolymer (Lys-biodynamer) obtained from Lys-hydrazide and $PEG_6$ylated carbazole dicarboxaldehyde. The y-axis shows the average $D_H$ (±standard deviation) determined by DLS.

It was found that the copolymers formed nanoparticles in solution. The hydrodynamic diameter ($D_H$) of the nanoparticles was determined using DLS. As shown in FIG. 1, at a pH of 7.4 (10 mM phosphate buffer) the $D_H$ of the nanoparticles was independent of the concentration of the copolymers in the solution. In contrast, at a pH of 5.0 (in 10 mM acetate buffer) the Z-average hydrodynamic diameter $D_H$ of the nanoparticles decreased with decreasing concentration of MDs. Thus, there is degradation of the copolymer at acidic conditions whereas the copolymer is stable at neutral pH values.

Formation of Polymer-Cargo-Complexes Comprising the Copolymer and Nucleic Acid or Peptide Cargo Molecules The $D_H$ substantially increased upon addition of nucleic acids (mCherry mRNA) or peptides (albumin-fluorescein isothiocyanate conjugate), indicating formation of polymer-cargo-complexes comprising the copolymer and nucleic acid or peptide cargo molecules, respectively.

Polymer-cargo-complexes of the invention having nucleic acids as cargo molecules may also be termed polyplexes. Polyplex formation was done in deionized water. The $D_H$ was determined to be about 120 nm by DLS with a polydispersity index (PDI) of 0.174 (FIG. 5A).

Notably, the $D_H$ was substantially constant between about 100 nm and about 200 nm at different copolymer concentrations at pH 7.4. In contrast, the $D_H$ substantially increased with decreasing nanoparticle concentration at pH 5.0 up to almost 900 nm at a concentration of 3.1 μg/ml. This indicates that controlled release of the cargo is possible at low pH. The results are shown in FIG. 3.

Regarding polymer-cargo-complexes having albumin-fluorescein isothiocyanate conjugate as peptide cargo molecule, the $D_H$ was determined to be about 244 nm by DLS with a polydispersity index (PDI) of 0.333 (FIG. 5B).

To further confirm the potential of polymer-cargo-complexes as a therapeutic protein carrier, complex formation was tested using insulin as cargo molecule. Insulin is a peptide hormone available as a therapeutic protein for diabetes. Positively charged Arg-Phe-biodynamer (RF-biodynamer) formed polymer-cargo-complexes with negatively charged insulin. FIG. 7 is a dynamic light scattering result showing hydrodynamic size and size distribution of the respective polymer-cargo-complexes.

Low Cytotoxicity

Cytotoxicity was tested in A549 cells using the MTT assay. Copolymers based on Lys, His or Arg derivatives were compared with prior art reagents PEI.

Different concentrations of the reagents were incubated with A549 cells (10,000 cells per well in 96 well plates) for 24 hours. The results are shown in FIG. 2 as average±standard deviation. The copolymers of the invention have strongly reduced cytotoxicity as compared to the prior art.

High Transfection Efficiency

A549 cells (100,000 cells per well) were incubated for 2 hours with different transfection reagents (present invention and prior art) comprising nucleic acids corresponding to 0.5 μg mRNA per well. The mRNA used was mCherry mRNA. Subsequently, the cells were washed and further incubated for 24 hours in a cell culture medium (10% FCS (fetal calf serum) containing RPMI (Roswell Park Memorial Institute) 1640 medium) for protein expression, then followed by flow cytometry measurement for evaluation of transfection efficiency and cell viability. Transfection efficiency was assessed by mCherry fluorescence. Cell viability was assessed using an amine reactive dye (DAPI (4',6-diamidine-2'-phenylindole dihydrochloride)) resulting in weakly stained nonpermeable live cells and more highly fluorescent dead cells due to increased permeability of the membranes.

Buffer and mRNA without transfection agents were used as negative controls.

PEI (polyethylene imine, cationic polymeric transfection agent) was used as prior art control. Copolymers of the present invention were tested as follows:

200 μg/mL copolymers, 20 NP ratio based on Lys derivatives (20 Lys-BDy),

200 μg/mL copolymers, 20 NP ratio based on mixture of Lys, His and Arg derivatives (20 KHR-BDy), Regarding KHR-BDy, the molar fractions of Lys, His and Arg were, 40%, 30% and 30%, respectively.

The results are shown in FIG. 4. Significant transfection was calculated by multiplying the percentage of transfected cells with the percentage of viable cells. For example, if 50% of viable cells are transfected and viability is 80%, the significant transfection is 0.50.8=0.4=40%. Thus, the significant transfection indicates the percentage of transfected cells based on the total cell number (dead+alive). Cytotoxicity is an important parameter when evaluating the transfection efficiency, not only because of further in vivo application but also because the toxicity affects actual transfection efficiency. The present invention is particularly advantageous based on the low toxicity and high significant transfection efficiency.

In fact, the significant transfection is about 20 times higher as compared to PEI (the gold standard of polymeric transfection agents) considering 20 Lys-BDy and 20 KHR-BDy. Notably, particularly high significant transfection efficiency was achieved with 20 KHR-BDy, thus with copolymer comprising derivatives of Lys, His and Arg.

Transfection of Dendritic Cells

To test the potential of polymer-cargo-complexes as a vaccine, the transfection ability and toxicity was tested using dendritic cells (DC2.4). The results are shown in FIG. 6.

Dendritic cells are one of the major antigen-presenting cells, processing antigen material and present it on the cell surface to the T cells of the immune system.

As a polymer-cargo-complex, mCherry encoding mRNA was complexed with KHR-BDy.

The polymer-cargo-complexes transfected dendritic cells with a transfection efficiency of 100%.

The toxicity was varied by the transfection condition. When the transfection condition was closer to the physiological condition, cell viability increased. The DC2.4 cell viability was 20% in an isotonic buffer (HBSS) but increased up to 79% in cell culture media (RPMI-1640) containing 10% of serum protein (fetal calf serum, FCS). Thus, the polymer-cargo-complexes of the present invention are particularly effective under physiological conditions indicating their suitability as vaccines.

Formation of Polymer-Cargo-Complexes of the Copolymer and siRNA Cargo Molecules

Complex formation of the copolymer was tested using siRNA as cargo molecule. siRNA has a potential for cancer treatment, and gene therapy by regulating protein expressions of target cells.

Lys-biodynamer formed polymer-cargo-complexes having a hydrodynamic diameter of 150 nm to 230 nm with a model siRNA, alexa-594-conjugated siRNA. The results are shown in FIG. 8A.

Encapsulation efficiency was dependent on the NP ratio as shown in FIG. 8B.

At 20 NP ratio, the encapsulation efficiency reached up to 80%. The encapsulation efficiency is determined as the weight percentage of cargo molecules forming polymer-cargo complexes with the biodynamer. Thus, encapsulation efficiency=weight of successfully complexed cargo molecules divided by total weight of cargo molecules.

Cell-Uptake of Polymer-Cargo-Complexes

Cellular uptake of the polymer-cargo-complexes formed from Lys-biodynamer and siRNA cargo molecules was tested using A549 cells.

The uptake increased with increased crosslinking ratio. By adding 50 w % of glutaraldehyde, the uptake increased to 84%. Thus, the polymer-cargo-complexes of the invention are suitable for delivering siRNA into cells. Differences in cell-uptake efficiency by NP ratio were not significant.

The results are shown in FIG. 9.

What is claimed is:

1. A polymer-cargo-complex, comprising:

a) a cross-linked copolymer, the copolymer comprising two alternating units A and B forming a repeat unit A-B such that the copolymer comprises a $(A\text{-}B)_n$ backbone with n being the number of repeat units of the backbone, wherein unit A is a derivative of an amino acid hydrazide and unit B is a derivate of a dialdehyde comprising a polyethylene glycol (PEG) group according to the following scheme:

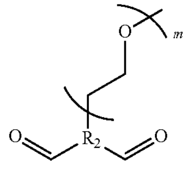

wherein $R_2$ is selected from the group consisting of a carbazole, a pyrrole derivative, a benzyl group, and an alkyl group, and wherein m is an integer from 3 to 12, wherein 40 to 100 mol % of unit A are derivatives of hydrazides of either cationic amino acids selected from the group consisting of lysine (Lys), arginine (Arg), histidine (His) and combinations of two or more thereof, or anionic amino acids selected from the group consisting of aspartic acid (Asp), glutamic acid (Glu) and combinations thereof, wherein the copolymer comprises imine groups and acylhydrazone groups alternatingly linking together the alternating units A and B of the polymer backbone such that the units A and B of the backbone are each linked to one neighboring unit by an imine group and to the other neighboring unit by an acylhydrazone group, and b) cargo molecules bound to the cross-linked copolymer by electrostatic interactions between the cargo molecules and the amino acid side chains of unit A, wherein the copolymer comprises cross-linking groups linking together some distinct units A present such that one cross-linking group links together two units A.

2. The polymer-cargo-complex according to claim 1, wherein the ratio of the total number of cross-linking groups to the total number of units A of the polymer is in a range of 0.05:1 to 0.45:1.

3. The polymer-cargo-complex according to claim 1, wherein the cargo molecule is selected from the group consisting of nucleic acids and peptides.

4. The polymer-cargo-complex according to claim 1, wherein the dialdehyde comprising a PEG group is a carbazole dicarboxaldehyde comprising a PEG group.

5. The polymer-cargo-complex according to claim 1, wherein 0 to 60 mol % of unit A are derivatives of hydrazides of amino acids selected from the group consisting of serine (Ser), threonine (Thr), asparagine (Asn), glutamine (Gln), cysteine (Cys), glycine (Gly), proline (Pro), alanine (Ala), valine (Val), isoleucine (Ile), leucine (Leu), methionine (Met), phenylalanine (Phe), tyrosine (Tyr), tryptophan (Trp) and combinations of two or more thereof.

6. The polymer-cargo-complex according to claim 1, wherein the polymer-cargo-complex is a nanoparticle having a hydrodynamic diameter ($D_H$) in a range of from 50 nm to 350 nm.

7. A non-therapeutic method, comprising the step of: performing transfection with the polymer-cargo-complex of claim 1.

8. A method, comprising the step of: performing therapy with the polymer-cargo-complex of claim 1.

9. A method, comprising the step of: performing gene therapy or peptide drug delivery with the polymer-cargo-complex according to claim 8.

10. A method, comprising the step of: performing treatment and/or prevention of viral diseases with the polymer-cargo-complex according to claim 8.

11. A kit comprising the polymer-cargo-complex of claim 1, or amino acid hydrazides and dialdehydes comprising a PEG group for preparing said polymer-cargo-complex.

12. A method of preparing a polymer-cargo-complex according to claim 1 comprising the following steps:

a) Providing an aqueous solution comprising (i) hydrazides of amino acids and (ii) dialdehydes comprising a PEG group, wherein the solution has a pH in the range of from 2 to 6, and wherein 40 to 100 mol % of the hydrazides are hydrazides of either cationic amino acids selected from the group consisting of lysine, arginine, histidine and combinations of two or more thereof, or anionic amino acids selected from the group consisting of aspartic acid, glutamic acid and combinations thereof, b) Incubating the solution to allow copolymer formation, c) Mixing the formed copolymer with a cargo molecule in an aqueous solution, d) Optionally adding amino acid side chain-specific cross-linker to the solution, e) Increase the pH of the solution to at least 7.

13. The method according to claim 12, wherein the cargo molecules of step c) are nucleotides, and wherein the nucleotides are added such that a molar ratio of amine groups to phosphate groups is from 1 to 50.

14. The polymer-cargo-complex according to claim 1, wherein the ratio of the total number of cross-linking groups to the total number of units A of the polymer is in a range of 0.05:1 to 0.5:1.

* * * * *